(12) United States Patent
Metzger et al.

(10) Patent No.: US 8,070,752 B2
(45) Date of Patent: Dec. 6, 2011

(54) PATIENT SPECIFIC ALIGNMENT GUIDE AND INTER-OPERATIVE ADJUSTMENT

(75) Inventors: Robert Metzger, Wakarusa, IN (US); Keith R. Berend, Columbus, OH (US); Michael E. Berend, Indianapolis, IN (US); Adolph V. Lombardi, Jr., New Albany, OH (US); Lance D. Perry, Warsaw, IN (US); Ryan J. Schoenefeld, Fort Wayne, IN (US); Radu Serban, Warsaw, IN (US); Thomas Donaldson, Redlands, CA (US)

(73) Assignee: Biomet Manufacturing Corp., Warsaw, IN (US)

( * ) Notice: Subject to any disclaimer, the term of this patent is extended or adjusted under 35 U.S.C. 154(b) by 885 days.

(21) Appl. No.: 11/971,390

(22) Filed: Jan. 9, 2008

(65) Prior Publication Data
US 2008/0312659 A1 Dec. 18, 2008

Related U.S. Application Data

(63) Continuation-in-part of application No. 11/756,057, filed on May 31, 2007, and a continuation-in-part of application No. 11/363,548, filed on Feb. 27, 2006, now Pat. No. 7,780,672.

(60) Provisional application No. 60/812,694, filed on Jun. 9, 2006.

(51) Int. Cl.
*A61B 17/58* (2006.01)
*A61B 17/60* (2006.01)
*A61F 2/00* (2006.01)

(52) U.S. Cl. .......................... 606/88; 606/86 R; 606/87

(58) Field of Classification Search .................. 606/87, 606/88
See application file for complete search history.

(56) References Cited

U.S. PATENT DOCUMENTS

| | | | |
|---|---|---|---|
| 1,480,285 A | 1/1924 | Moore |
| 1,763,730 A | 6/1930 | Von Lackum |
| 1,959,615 A | 5/1934 | Derrah |
| 2,407,845 A | 9/1946 | Nemeyer |
| 2,433,815 A | 12/1947 | LaForge |
| 2,455,655 A | 12/1948 | Carroll |
| 2,618,913 A | 11/1952 | Plancon et al. |
| 2,702,550 A | 2/1955 | Rowe |
| 2,724,326 A | 11/1955 | Long |
| 2,910,978 A | 11/1959 | Urist |
| 2,955,530 A | 10/1960 | Nilo |

(Continued)

FOREIGN PATENT DOCUMENTS

CA 2447694 A1 12/2002

(Continued)

OTHER PUBLICATIONS

"AGC 3000 Intramedullary Surgical Technique Using PMMA Fixation," 1987, Biomet, Inc.

(Continued)

*Primary Examiner* — Thomas C. Barrett
*Assistant Examiner* — Christine Nelson
(74) *Attorney, Agent, or Firm* — Harness, Dickey

(57) ABSTRACT

A method of preparing a joint for a prosthesis in a patient. The method includes obtaining scan data associated with the joint of the patient, preparing a three-dimensional image of the joint based on the scan data, preparing a pre-operative surgical plan based on the scan data, and preparing an image of a patient-specific alignment guide, and intra-operatively modifying the surgical plan.

13 Claims, 20 Drawing Sheets

U.S. PATENT DOCUMENTS

| | | |
|---|---|---|
| 3,048,522 A | 8/1962 | Velley |
| 3,229,006 A | 1/1966 | Nohl |
| 3,514,791 A | 6/1970 | Sparks |
| 3,554,197 A | 1/1971 | Dobbie |
| 3,624,747 A | 11/1971 | McKnight et al. |
| 3,631,596 A | 1/1972 | Glaus |
| 3,678,934 A | 7/1972 | Warfield et al. |
| 3,698,017 A | 10/1972 | Scales et al. |
| 3,703,036 A | 11/1972 | Karubian |
| 3,774,244 A | 11/1973 | Walker |
| 3,783,873 A | 1/1974 | Jacobs |
| 3,807,393 A | 4/1974 | McDonald |
| 3,811,449 A | 5/1974 | Gravlee et al. |
| 3,840,904 A | 10/1974 | Tronzo |
| 3,869,731 A | 3/1975 | Waugh et al. |
| 3,903,549 A | 9/1975 | Deyerle |
| 3,905,105 A | 9/1975 | Tuke |
| 3,905,374 A | 9/1975 | Winter |
| 3,911,923 A | 10/1975 | Yoon |
| 3,913,585 A | 10/1975 | Wolvek |
| 3,920,022 A | 11/1975 | Pastor |
| 3,941,127 A | 3/1976 | Froning |
| 3,967,625 A | 7/1976 | Yoon |
| 3,989,049 A | 11/1976 | Yoon |
| 3,991,426 A | 11/1976 | Flom et al. |
| 3,994,287 A | 11/1976 | Turp et al. |
| 4,053,953 A | 10/1977 | Flom et al. |
| 4,055,862 A | 11/1977 | Farling |
| 4,081,866 A | 4/1978 | Upshaw et al. |
| 4,085,466 A | 4/1978 | Goodfellow et al. |
| 4,085,743 A | 4/1978 | Yoon |
| 4,103,680 A | 8/1978 | Yoon |
| 4,299,224 A | 11/1981 | Noiles |
| 4,304,178 A | 12/1981 | Haberle |
| 4,311,145 A | 1/1982 | Esty et al. |
| 4,324,006 A | 4/1982 | Charnley |
| 4,344,193 A | 8/1982 | Kenny |
| 4,349,018 A | 9/1982 | Chambers |
| 4,373,709 A | 2/1983 | Whitt |
| 4,374,523 A | 2/1983 | Yoon |
| 4,385,404 A | 5/1983 | Sully et al. |
| 4,386,609 A | 6/1983 | Mongeon |
| 4,400,833 A | 8/1983 | Kurland |
| 4,436,684 A | 3/1984 | White |
| D273,895 S | 5/1984 | Kenna |
| D274,091 S | 5/1984 | Kenna |
| 4,453,421 A | 6/1984 | Umano |
| 4,475,549 A | 10/1984 | Oh |
| 4,501,269 A | 2/1985 | Bagby |
| 4,506,393 A | 3/1985 | Murphy |
| 4,509,518 A | 4/1985 | McGarry et al. |
| 4,516,276 A | 5/1985 | Mittelmeier et al. |
| 4,534,365 A | 8/1985 | Bonetta et al. |
| 4,545,375 A | 10/1985 | Cline |
| 4,554,686 A | 11/1985 | Baker |
| 4,562,598 A | 1/1986 | Kranz |
| 4,565,192 A | 1/1986 | Shapiro |
| 4,567,886 A | 2/1986 | Petersen |
| 4,574,794 A | 3/1986 | Cooke et al. |
| 4,619,391 A | 10/1986 | Sharkany et al. |
| 4,619,658 A | 10/1986 | Pappas et al. |
| 4,621,630 A | 11/1986 | Kenna |
| 4,624,254 A | 11/1986 | McGarry et al. |
| 4,632,111 A | 12/1986 | Roche |
| 4,641,648 A | 2/1987 | Shapiro |
| 4,642,120 A | 2/1987 | Nevo et al. |
| 4,646,729 A | 3/1987 | Kenna et al. |
| 4,662,372 A | 5/1987 | Sharkany et al. |
| 4,663,720 A | 5/1987 | Duret et al. |
| 4,678,470 A | 7/1987 | Nashef et al. |
| 4,682,598 A | 7/1987 | Beraha |
| 4,685,460 A | 8/1987 | Thornton |
| 4,695,283 A | 9/1987 | Aldinger |
| 4,703,751 A | 11/1987 | Pohl |
| 4,704,686 A | 11/1987 | Aldinger |
| 4,711,233 A | 12/1987 | Brown |
| 4,718,413 A | 1/1988 | Johnson |
| 4,718,916 A | 1/1988 | Morscher |
| 4,721,104 A | 1/1988 | Kaufman et al. |
| 4,739,751 A | 4/1988 | Sapega et al. |
| 4,778,474 A | 10/1988 | Homsy |
| 4,794,854 A | 1/1989 | Swaim |
| 4,800,874 A | 1/1989 | David et al. |
| 4,817,602 A | 4/1989 | Beraha |
| 4,821,213 A | 4/1989 | Cline et al. |
| 4,822,365 A | 4/1989 | Walker et al. |
| 4,834,757 A | 5/1989 | Brantigan |
| 4,838,891 A | 6/1989 | Branemark et al. |
| 4,841,975 A | 6/1989 | Woolson |
| 4,846,161 A | 7/1989 | Roger |
| 4,863,472 A | 9/1989 | Tormala et al. |
| 4,871,975 A | 10/1989 | Nawata et al. |
| 4,888,022 A | 12/1989 | Huebsch |
| 4,893,619 A | 1/1990 | Dale et al. |
| 4,896,663 A | 1/1990 | Vandewalls |
| 4,911,721 A | 3/1990 | Andergaten et al. |
| 4,927,422 A | 5/1990 | Engelhardt |
| 4,935,023 A | 6/1990 | Whiteside et al. |
| 4,936,852 A | 6/1990 | Kent et al. |
| 4,936,862 A | 6/1990 | Walker et al. |
| 4,950,296 A | 8/1990 | McIntyre |
| 4,952,213 A | 8/1990 | Bowman et al. |
| 4,959,066 A | 9/1990 | Dunn et al. |
| 4,961,740 A | 10/1990 | Ray et al. |
| 4,961,954 A | 10/1990 | Goldberg et al. |
| 4,964,865 A | 10/1990 | Burkhead et al. |
| 4,976,737 A | 12/1990 | Leake |
| 4,979,949 A | 12/1990 | Matsen, III et al. |
| 4,979,957 A | 12/1990 | Hodorek |
| 4,985,037 A | 1/1991 | Petersen |
| 4,985,038 A | 1/1991 | Lyell |
| 5,002,579 A | 3/1991 | Copf et al. |
| 5,007,912 A | 4/1991 | Albrektsson et al. |
| 5,007,936 A | 4/1991 | Woolson |
| 5,015,247 A | 5/1991 | Michelson |
| 5,030,221 A | 7/1991 | Buechel et al. |
| 5,032,132 A | 7/1991 | Matsen, III et al. |
| 5,035,700 A | 7/1991 | Kenna |
| 5,041,117 A | 8/1991 | Engelhardt |
| 5,053,039 A | 10/1991 | Hofmann et al. |
| 5,060,678 A | 10/1991 | Bauman et al. |
| 5,061,286 A | 10/1991 | Lyle |
| 5,062,843 A | 11/1991 | Mahony, III |
| 5,073,373 A | 12/1991 | O'Leary et al. |
| 5,082,670 A | 1/1992 | Gage et al. |
| 5,084,050 A | 1/1992 | Draenert |
| 5,086,401 A | 2/1992 | Glassman et al. |
| 5,092,869 A | 3/1992 | Waldron |
| 5,098,383 A | 3/1992 | Hemmy et al. |
| 5,098,436 A | 3/1992 | Ferrante et al. |
| 5,098,437 A | 3/1992 | Kashuba et al. |
| 5,099,859 A | 3/1992 | Bell |
| 5,100,689 A | 3/1992 | Goldberg et al. |
| 5,101,720 A | 4/1992 | Bianchi |
| 5,108,425 A | 4/1992 | Hwang |
| 5,108,441 A | 4/1992 | McDowell |
| 5,111,987 A | 5/1992 | Moeinzadeh et al. |
| 5,122,144 A | 6/1992 | Bert et al. |
| 5,123,906 A | 6/1992 | Kelman |
| 5,129,908 A | 7/1992 | Petersen |
| 5,129,909 A | 7/1992 | Sutherland |
| 5,133,760 A | 7/1992 | Petersen et al. |
| 5,140,777 A | 8/1992 | Ushiyama et al. |
| 5,147,365 A | 9/1992 | Whitlock et al. |
| 5,150,304 A | 9/1992 | Berchem et al. |
| 5,152,744 A | 10/1992 | Krause et al. |
| 5,152,778 A | 10/1992 | Bales, Jr. et al. |
| 5,154,717 A | 10/1992 | Matsen, III et al. |
| 5,162,506 A | 11/1992 | Hadden |
| 5,163,949 A | 11/1992 | Bonutti |
| 5,170,800 A | 12/1992 | Smith et al. |
| 5,171,243 A | 12/1992 | Kashuba et al. |
| 5,171,244 A | 12/1992 | Caspari et al. |
| 5,171,276 A | 12/1992 | Caspari et al. |
| 5,174,300 A | 12/1992 | Bales et al. |
| 5,176,684 A | 1/1993 | Ferrante et al. |
| 5,176,702 A | 1/1993 | Bales et al. |

| Patent No. | Date | Inventor |
|---|---|---|
| 5,178,622 A | 1/1993 | Lehner, II |
| 5,183,053 A | 2/1993 | Yeh et al. |
| 5,183,464 A | 2/1993 | Dubrul et al. |
| 5,186,178 A | 2/1993 | Yeh et al. |
| 5,192,327 A | 3/1993 | Brantigan |
| 5,197,968 A | 3/1993 | Clement |
| 5,197,971 A | 3/1993 | Bonutti |
| 5,197,987 A | 3/1993 | Koch et al. |
| 5,204,106 A | 4/1993 | Schepers et al. |
| 5,207,680 A | 5/1993 | Dietz et al. |
| 5,207,692 A | 5/1993 | Kraus et al. |
| 5,217,463 A | 6/1993 | Michael |
| 5,228,459 A | 7/1993 | Caspari et al. |
| 5,234,433 A | 8/1993 | Bert et al. |
| 5,242,448 A | 9/1993 | Pettine et al. |
| 5,258,004 A | 11/1993 | Bales et al. |
| 5,258,032 A | 11/1993 | Bertin |
| 5,261,915 A | 11/1993 | Durlacher et al. |
| 5,263,498 A | 11/1993 | Caspari et al. |
| 5,263,987 A | 11/1993 | Shah |
| 5,269,785 A | 12/1993 | Bonutti |
| 5,273,524 A | 12/1993 | Fox et al. |
| 5,274,565 A | 12/1993 | Reuben |
| D343,247 S | 1/1994 | Walen |
| 5,275,166 A | 1/1994 | Vaitekunas et al. |
| 5,275,603 A | 1/1994 | Ferrante et al. |
| 5,282,803 A | 2/1994 | Lackey |
| 5,285,773 A | 2/1994 | Bonutti et al. |
| 5,293,878 A | 3/1994 | Bales et al. |
| 5,295,994 A | 3/1994 | Bonutti |
| 5,299,288 A | 3/1994 | Glassman et al. |
| 5,300,077 A | 4/1994 | Howell |
| 5,304,181 A | 4/1994 | Caspari et al. |
| 5,306,285 A | 4/1994 | Miller et al. |
| 5,308,349 A | 5/1994 | Mikhail |
| 5,314,482 A | 5/1994 | Goodfellow et al. |
| 5,320,625 A | 6/1994 | Bertin |
| 5,322,505 A | 6/1994 | Krause et al. |
| 5,329,845 A | 7/1994 | Bichel |
| 5,342,366 A | 8/1994 | Whiteside et al. |
| 5,342,367 A | 8/1994 | Ferrante et al. |
| 5,342,368 A | 8/1994 | Petersen |
| 5,344,423 A | 9/1994 | Dietz et al. |
| 5,344,458 A | 9/1994 | Bonutti |
| 5,348,541 A | 9/1994 | Lyell |
| 5,360,446 A | 11/1994 | Kennedy |
| 5,364,402 A | 11/1994 | Mumme et al. |
| 5,368,599 A | 11/1994 | Hirsch et al. |
| 5,368,858 A | 11/1994 | Hunziker |
| 5,370,692 A | 12/1994 | Fink et al. |
| 5,370,699 A | 12/1994 | Hood et al. |
| 5,379,133 A | 1/1995 | Kirk |
| 5,382,249 A | 1/1995 | Fletcher |
| 5,383,937 A | 1/1995 | Mikhail |
| 5,390,683 A | 2/1995 | Pisharodi |
| 5,395,376 A | 3/1995 | Caspari et al. |
| 5,405,395 A | 4/1995 | Coates |
| 5,408,409 A | 4/1995 | Glassman et al. |
| D358,647 S | 5/1995 | Cohen et al. |
| 5,415,662 A | 5/1995 | Ferrante et al. |
| 5,423,827 A | 6/1995 | Mumme et al. |
| 5,425,355 A | 6/1995 | Kulick |
| 5,425,745 A | 6/1995 | Green et al. |
| 5,438,263 A | 8/1995 | Dworkin et al. |
| 5,440,496 A | 8/1995 | Andersson et al. |
| 5,443,475 A | 8/1995 | Auerbach et al. |
| 5,445,639 A | 8/1995 | Kuslich et al. |
| 5,445,642 A | 8/1995 | McNulty et al. |
| 5,448,489 A | 9/1995 | Reuben |
| 5,452,407 A | 9/1995 | Crook |
| 5,454,365 A | 10/1995 | Bonutti |
| 5,454,815 A | 10/1995 | Geisser et al. |
| 5,454,816 A | 10/1995 | Ashby |
| 5,456,268 A | 10/1995 | Bonutti |
| 5,472,415 A | 12/1995 | King et al. |
| 5,474,559 A | 12/1995 | Bertin et al. |
| 5,484,095 A | 1/1996 | Green et al. |
| 5,486,178 A | 1/1996 | Hodge |
| 5,490,854 A | 2/1996 | Fisher et al. |
| 5,496,324 A | 3/1996 | Barnes |
| 5,497,933 A | 3/1996 | DeFonzo et al. |
| 5,507,763 A | 4/1996 | Petersen et al. |
| 5,507,833 A | 4/1996 | Bohn |
| 5,514,139 A | 5/1996 | Goldstein et al. |
| 5,514,143 A | 5/1996 | Bonutti et al. |
| 5,514,519 A | 5/1996 | Neckers |
| 5,520,692 A | 5/1996 | Ferrante |
| 5,520,694 A | 5/1996 | Dance et al. |
| 5,522,897 A | 6/1996 | King et al. |
| 5,527,317 A | 6/1996 | Ashby et al. |
| 5,539,649 A | 7/1996 | Walsh et al. |
| 5,540,695 A | 7/1996 | Levy |
| 5,545,222 A | 8/1996 | Bonutti |
| 5,546,720 A | 8/1996 | LaBruzza |
| 5,549,683 A | 8/1996 | Bonutti |
| 5,554,169 A | 9/1996 | Green et al. |
| 5,554,190 A | 9/1996 | Draenert |
| 5,560,096 A | 10/1996 | Stephens |
| 5,562,675 A | 10/1996 | McNulty et al. |
| 5,569,163 A | 10/1996 | Francis et al. |
| 5,569,261 A | 10/1996 | Marik et al. |
| 5,570,700 A | 11/1996 | Vogeler |
| 5,571,110 A | 11/1996 | Matsen, III et al. |
| 5,578,037 A | 11/1996 | Sanders et al. |
| 5,578,039 A | 11/1996 | Vendrely et al. |
| 5,593,448 A | 1/1997 | Dong |
| 5,595,703 A | 1/1997 | Swaelens et al. |
| 5,597,379 A | 1/1997 | Haines et al. |
| 5,607,431 A | 3/1997 | Dudasik et al. |
| 5,608,052 A | 3/1997 | Zmitek et al. |
| 5,609,603 A | 3/1997 | Linden |
| 5,620,448 A | 4/1997 | Puddu |
| 5,624,444 A | 4/1997 | Wixon et al. |
| 5,624,463 A | 4/1997 | Stone et al. |
| 5,632,745 A | 5/1997 | Schwartz |
| 5,634,927 A | 6/1997 | Houston et al. |
| 5,643,272 A | 7/1997 | Haines et al. |
| 5,649,946 A | 7/1997 | Bramlet |
| 5,649,947 A | 7/1997 | Auerbach et al. |
| 5,653,714 A | 8/1997 | Dietz et al. |
| 5,658,294 A | 8/1997 | Sederholm |
| 5,659,947 A | 8/1997 | Eilers et al. |
| 5,662,656 A | 9/1997 | White |
| 5,662,710 A | 9/1997 | Bonutti |
| 5,667,069 A | 9/1997 | Williams, Jr. |
| 5,667,511 A | 9/1997 | Vendrely et al. |
| 5,667,512 A | 9/1997 | Johnson |
| 5,667,520 A | 9/1997 | Bonutti |
| D385,163 S | 10/1997 | Hutchins et al. |
| 5,677,107 A | 10/1997 | Neckers |
| 5,681,316 A | 10/1997 | DeOrio et al. |
| 5,681,354 A | 10/1997 | Eckhoff |
| 5,682,886 A | 11/1997 | Delp et al. |
| 5,683,398 A | 11/1997 | Carls et al. |
| 5,688,279 A | 11/1997 | McNulty et al. |
| 5,688,280 A | 11/1997 | Booth, Jr. et al. |
| 5,690,635 A | 11/1997 | Matsen, III et al. |
| 5,694,693 A | 12/1997 | Hutchins et al. |
| 5,702,447 A | 12/1997 | Walch et al. |
| 5,702,460 A | 12/1997 | Carls et al. |
| 5,702,475 A | 12/1997 | Zahedi |
| 5,704,941 A | 1/1998 | Jacober et al. |
| 5,707,350 A | 1/1998 | Krause et al. |
| 5,712,543 A | 1/1998 | Sjostrom |
| 5,716,360 A | 2/1998 | Baldwin et al. |
| 5,718,708 A | 2/1998 | Webb |
| 5,720,752 A | 2/1998 | Elliott et al. |
| 5,722,978 A | 3/1998 | Jenkins, Jr. |
| 5,723,331 A | 3/1998 | Tubo et al. |
| 5,725,376 A | 3/1998 | Poirier |
| 5,725,593 A | 3/1998 | Caracciolo |
| 5,733,292 A | 3/1998 | Gustilo et al. |
| 5,735,277 A | 4/1998 | Schuster |
| 5,748,767 A | 5/1998 | Raab |
| 5,749,875 A | 5/1998 | Puddu |
| 5,749,876 A | 5/1998 | Duvillier et al. |
| 5,755,731 A | 5/1998 | Grinberg |
| 5,755,791 A | 5/1998 | Whitson et al. |

| | | | | | | |
|---|---|---|---|---|---|---|
| 5,755,803 | A | 5/1998 | Haines et al. | 6,171,340 B1 | 1/2001 | McDowell |
| 5,762,125 | A | 6/1998 | Mastrorio | 6,174,321 B1 | 1/2001 | Webb |
| 5,768,134 | A | 6/1998 | Swaelens et al. | 6,185,315 B1 | 2/2001 | Schmucker et al. |
| 5,769,855 | A | 6/1998 | Bertin et al. | 6,187,010 B1 | 2/2001 | Masini |
| 5,769,899 | A | 6/1998 | Schwartz et al. | 6,187,023 B1 | 2/2001 | Bonutti |
| 5,772,594 | A | 6/1998 | Barrick | 6,195,158 B1 | 2/2001 | Cadell et al. |
| 5,786,217 | A | 7/1998 | Tubo et al. | 6,195,615 B1 | 2/2001 | Lysen |
| 5,788,700 | A | 8/1998 | Morawa et al. | 6,197,064 B1 | 3/2001 | Haines et al. |
| 5,792,143 | A | 8/1998 | Samuelson et al. | 6,198,794 B1 | 3/2001 | Peshkin et al. |
| 5,798,924 | A | 8/1998 | Eufinger et al. | 6,205,411 B1 | 3/2001 | DiGioia, III et al. |
| 5,799,055 | A | 8/1998 | Peshkin et al. | 6,206,927 B1 | 3/2001 | Fell et al. |
| 5,810,827 | A | 9/1998 | Haines et al. | 6,211,976 B1 | 4/2001 | Popovich et al. |
| 5,810,831 | A | 9/1998 | D'Antonio | 6,214,051 B1 | 4/2001 | Badorf et al. |
| 5,817,097 | A | 10/1998 | Howard et al. | 6,228,121 B1 | 5/2001 | Khalili |
| 5,817,109 | A | 10/1998 | McGarry et al. | 6,254,604 B1 | 7/2001 | Howell |
| 5,842,477 | A | 12/1998 | Naughton et al. | 6,258,097 B1 | 7/2001 | Cook et al. |
| 5,846,931 | A | 12/1998 | Hattersley et al. | 6,258,127 B1 | 7/2001 | Schmotzer |
| 5,860,980 | A | 1/1999 | Axelson, Jr. et al. | 6,264,698 B1 | 7/2001 | Lawes et al. |
| 5,860,981 | A | 1/1999 | Bertin et al. | 6,273,891 B1 | 8/2001 | Masini |
| 5,866,415 | A | 2/1999 | Villeneuve | 6,277,136 B1 | 8/2001 | Bonutti |
| 5,871,018 | A | 2/1999 | Delp et al. | 6,290,703 B1 | 9/2001 | Ganem |
| 5,871,493 | A | 2/1999 | Sjostrom et al. | 6,290,704 B1 | 9/2001 | Burkinshaw et al. |
| 5,876,456 | A | 3/1999 | Sederholm et al. | 6,290,727 B1 | 9/2001 | Otto et al. |
| 5,879,354 | A | 3/1999 | Haines et al. | 6,293,971 B1 | 9/2001 | Nelson et al. |
| 5,879,398 | A | 3/1999 | Swarts et al. | 6,312,473 B1 | 11/2001 | Oshida |
| 5,879,402 | A | 3/1999 | Lawes et al. | 6,319,285 B1 | 11/2001 | Chamier et al. |
| 5,880,976 | A | 3/1999 | DiGioia, III et al. | 6,325,806 B1 | 12/2001 | Fox |
| 5,885,297 | A | 3/1999 | Matsen, III | 6,325,829 B1 | 12/2001 | Schmotzer |
| 5,885,298 | A | 3/1999 | Herrington et al. | 6,328,572 B1 | 12/2001 | Higashida et al. |
| 5,888,219 | A | 3/1999 | Bonutti | 6,338,737 B1 | 1/2002 | Toledano |
| 5,895,389 | A | 4/1999 | Schenk et al. | 6,343,987 B2 | 2/2002 | Hayama et al. |
| 5,899,907 | A | 5/1999 | Johnson | 6,354,011 B1 | 3/2002 | Albrecht |
| 5,899,914 | A | 5/1999 | Zirps et al. | 6,358,266 B1 | 3/2002 | Bonutti |
| 5,901,060 | A | 5/1999 | Schall et al. | 6,361,565 B1 | 3/2002 | Bonutti |
| 5,908,424 | A | 6/1999 | Bertin et al. | 6,383,228 B1 | 5/2002 | Schmotzer |
| 5,911,723 | A | 6/1999 | Ashby et al. | 6,391,040 B1 | 5/2002 | Christoudias |
| 5,911,724 | A | 6/1999 | Wehrli | 6,391,251 B1 | 5/2002 | Keicher et al. |
| 5,913,874 | A | 6/1999 | Berns et al. | 6,395,005 B1 | 5/2002 | Lovell |
| 5,916,219 | A | 6/1999 | Matsuno et al. | 6,406,495 B1 | 6/2002 | Schoch |
| 5,921,990 | A | 7/1999 | Webb | 6,409,722 B1 | 6/2002 | Hoey et al. |
| 5,925,049 | A | 7/1999 | Gustilo et al. | 6,423,063 B1 | 7/2002 | Bonutti |
| 5,942,370 | A | 8/1999 | Neckers | 6,427,698 B1 | 8/2002 | Yoon |
| 5,961,499 | A | 10/1999 | Bonutti et al. | 6,431,743 B1 | 8/2002 | Mizutani et al. |
| 5,967,777 | A | 10/1999 | Klein et al. | D462,767 S | 9/2002 | Meyer et al. |
| 5,976,149 | A | 11/1999 | Masini | 6,458,135 B1 | 10/2002 | Harwin et al. |
| 5,997,566 | A | 12/1999 | Tobin | 6,459,948 B1 | 10/2002 | Ateshian et al. |
| 6,007,537 | A | 12/1999 | Burkinshaw et al. | 6,463,351 B1 | 10/2002 | Clynch |
| 6,012,456 | A | 1/2000 | Schuerch | 6,468,280 B1 | 10/2002 | Saenger et al. |
| 6,015,419 | A | 1/2000 | Strome et al. | 6,468,289 B1 | 10/2002 | Bonutti |
| 6,019,767 | A | 2/2000 | Howell | 6,478,799 B1 | 11/2002 | Williamson |
| 6,022,350 | A | 2/2000 | Ganem | 6,482,209 B1 | 11/2002 | Engh et al. |
| 6,024,746 | A | 2/2000 | Katz | 6,488,715 B1 | 12/2002 | Pope et al. |
| 6,033,415 | A | 3/2000 | Mittelstadt et al. | 6,500,181 B1 | 12/2002 | Portney |
| 6,056,754 | A | 5/2000 | Haines et al. | 6,503,255 B1 | 1/2003 | Albrektsson et al. |
| 6,056,756 | A | 5/2000 | Eng et al. | 6,503,267 B2 | 1/2003 | Bonutti et al. |
| 6,059,817 | A | 5/2000 | Bonutti et al. | 6,510,334 B1 | 1/2003 | Schuster et al. |
| 6,059,831 | A | 5/2000 | Braslow et al. | 6,514,259 B2 | 2/2003 | Picard et al. |
| 6,059,833 | A | 5/2000 | Doets | 6,517,583 B1 | 2/2003 | Pope et al. |
| 6,063,095 | A | 5/2000 | Wang et al. | 6,520,964 B2 | 2/2003 | Tallarida et al. |
| 6,077,270 | A | 6/2000 | Katz | 6,533,737 B1 | 3/2003 | Brosseau et al. |
| 6,077,287 | A | 6/2000 | Taylor et al. | 6,554,837 B1 | 4/2003 | Hauri et al. |
| 6,086,593 | A | 7/2000 | Bonutti | 6,554,838 B1 | 4/2003 | McGovern et al. |
| 6,090,122 | A | 7/2000 | Sjostrom et al. | 6,556,008 B2 | 4/2003 | Thesen |
| 6,096,043 | A | 8/2000 | Techiera et al. | 6,558,391 B2 | 5/2003 | Axelson, Jr. et al. |
| 6,099,531 | A | 8/2000 | Bonutti | 6,558,428 B2 | 5/2003 | Park |
| 6,099,532 | A | 8/2000 | Florea | 6,564,085 B2 | 5/2003 | Meaney et al. |
| 6,102,850 | A | 8/2000 | Wang et al. | 6,567,681 B2 | 5/2003 | Lindequist |
| 6,106,529 | A | 8/2000 | Techiera | 6,575,980 B1 | 6/2003 | Robie et al. |
| 6,118,845 | A | 9/2000 | Simon et al. | 6,575,982 B1 | 6/2003 | Bonutti |
| 6,120,509 | A | 9/2000 | Wheeler | 6,591,581 B2 | 7/2003 | Schmieding |
| 6,120,510 | A | 9/2000 | Albrektsson et al. | 6,602,259 B1 | 8/2003 | Masini |
| 6,120,544 | A | 9/2000 | Grundei et al. | 6,605,293 B1 | 8/2003 | Giordano et al. |
| 6,126,690 | A | 10/2000 | Ateshian et al. | 6,620,181 B1 | 9/2003 | Bonutti |
| 6,132,472 | A | 10/2000 | Bonutti | 6,622,567 B1 | 9/2003 | Hamel et al. |
| 6,136,033 | A | 10/2000 | Suemer | 6,629,999 B1 | 10/2003 | Serafin, Jr. |
| 6,156,069 | A | 12/2000 | Amstutz | 6,632,225 B2 | 10/2003 | Sanford et al. |
| 6,156,070 | A | 12/2000 | Incavo et al. | 6,635,073 B2 | 10/2003 | Bonutti |
| 6,159,246 | A | 12/2000 | Mendes et al. | 6,641,617 B1 | 11/2003 | Merrill et al. |
| 6,161,080 | A | 12/2000 | Aouni-Ateshian et al. | 6,673,077 B1 | 1/2004 | Katz |

| | | | | | |
|---|---|---|---|---|---|
| 6,676,662 B1 | 1/2004 | Bagga et al. | 7,591,821 B2 | 9/2009 | Kelman |
| 6,682,566 B2 | 1/2004 | Draenert | 7,601,155 B2 | 10/2009 | Petersen |
| 6,695,848 B2 | 2/2004 | Haines | 7,604,639 B2 | 10/2009 | Swanson |
| 6,696,073 B2 | 2/2004 | Boyce et al. | 7,611,516 B2 | 11/2009 | Maroney |
| 6,697,664 B2 | 2/2004 | Kienzle, III et al. | 7,618,451 B2 | 11/2009 | Berez et al. |
| 6,701,174 B1 | 3/2004 | Krause et al. | 7,621,915 B2 | 11/2009 | Frederick et al. |
| 6,702,821 B2 | 3/2004 | Bonutti | 7,625,409 B2 | 12/2009 | Saltzman et al. |
| 6,709,462 B2 | 3/2004 | Hanssen | 7,651,501 B2 | 1/2010 | Penenberg et al. |
| 6,711,431 B2 | 3/2004 | Sarin et al. | 7,682,398 B2 | 3/2010 | Croxton et al. |
| 6,711,432 B1 | 3/2004 | Krause et al. | 7,695,477 B2 | 4/2010 | Creger et al. |
| 6,712,856 B1 | 3/2004 | Carignan et al. | 7,695,521 B2 | 4/2010 | Ely et al. |
| 6,716,249 B2 | 4/2004 | Hyde | 7,704,253 B2 | 4/2010 | Bastian et al. |
| 6,725,077 B1 | 4/2004 | Balloni et al. | 7,794,504 B2 | 9/2010 | Case |
| 6,738,657 B1 | 5/2004 | Franklin et al. | 7,806,896 B1 | 10/2010 | Bonutti |
| 6,740,092 B2 | 5/2004 | Lombardo et al. | 7,819,925 B2 | 10/2010 | King et al. |
| 6,749,638 B1 | 6/2004 | Saladino | 7,828,806 B2 | 11/2010 | Graf et al. |
| 6,750,653 B1 | 6/2004 | Zou et al. | 7,896,921 B2 | 3/2011 | Smith et al. |
| 6,770,078 B2 | 8/2004 | Bonutti | 7,935,119 B2 | 5/2011 | Ammann et al. |
| 6,772,026 B2 | 8/2004 | Bradbury et al. | 7,938,861 B2 | 5/2011 | King et al. |
| 6,780,190 B2 | 8/2004 | Maroney | 7,963,968 B2 | 6/2011 | Dees, Jr. |
| 6,786,930 B2 | 9/2004 | Biscup | 2001/0005797 A1 | 6/2001 | Barlow et al. |
| 6,799,066 B2 | 9/2004 | Steines et al. | 2001/0011190 A1 | 8/2001 | Park |
| 6,827,723 B2 | 12/2004 | Carson | 2001/0018589 A1 | 8/2001 | Muller |
| 6,905,514 B2 | 6/2005 | Carignan et al. | 2001/0034554 A1 | 10/2001 | Pappas |
| 6,923,817 B2 | 8/2005 | Carson et al. | 2001/0037155 A1 | 11/2001 | Merchant |
| 6,923,831 B2 | 8/2005 | Fell et al. | 2002/0007294 A1 | 1/2002 | Bradbury et al. |
| 6,932,842 B1 | 8/2005 | Litschko et al. | 2002/0029038 A1 | 3/2002 | Haines |
| 6,942,475 B2 | 9/2005 | Ensign et al. | 2002/0029045 A1 | 3/2002 | Bonutti |
| 6,944,518 B2 | 9/2005 | Roose | 2002/0052606 A1 | 5/2002 | Bonutti |
| 6,945,976 B2 | 9/2005 | Ball et al. | 2002/0059049 A1 | 5/2002 | Bradbury et al. |
| 6,953,480 B2 | 10/2005 | Mears et al. | 2002/0082741 A1 | 6/2002 | Mazumder et al. |
| 6,979,299 B2 | 12/2005 | Peabody et al. | 2002/0087274 A1 | 7/2002 | Alexander et al. |
| 6,990,220 B2 | 1/2006 | Ellis et al. | 2002/0116023 A1 | 8/2002 | Fletcher et al. |
| 7,029,477 B2 | 4/2006 | Grimm | 2002/0147415 A1 | 10/2002 | Martelli |
| 7,029,479 B2 | 4/2006 | Tallarida et al. | 2002/0173797 A1 | 11/2002 | Van Zile et al. |
| 7,042,222 B2 | 5/2006 | Zheng et al. | 2002/0198529 A1 | 12/2002 | Masini |
| 7,048,741 B2 | 5/2006 | Swanson | 2002/0198531 A1 | 12/2002 | Millard et al. |
| 7,050,877 B2 | 5/2006 | Iseki et al. | 2003/0009234 A1 | 1/2003 | Treacy et al. |
| 7,060,074 B2 | 6/2006 | Rosa et al. | 2003/0011624 A1 | 1/2003 | Ellis |
| 7,074,241 B2 | 7/2006 | McKinnon | 2003/0018338 A1 | 1/2003 | Axelson et al. |
| RE39,301 E | 9/2006 | Bertin | 2003/0028196 A1 | 2/2003 | Bonutti |
| 7,104,997 B2 | 9/2006 | Lionberger et al. | 2003/0039676 A1 | 2/2003 | Boyce et al. |
| 7,105,026 B2 | 9/2006 | Johnson et al. | 2003/0055502 A1 | 3/2003 | Lang et al. |
| 7,115,131 B2 | 10/2006 | Engh et al. | 2003/0060831 A1 | 3/2003 | Bonutti |
| 7,141,053 B2 | 11/2006 | Rosa et al. | 2003/0100906 A1 | 5/2003 | Rosa et al. |
| 7,169,185 B2 | 1/2007 | Sidebotham | 2003/0100907 A1 | 5/2003 | Rosa et al. |
| 7,172,599 B2 | 2/2007 | Steffensmeier et al. | 2003/0109784 A1 | 6/2003 | Loh et al. |
| 7,176,466 B2 | 2/2007 | Rousso et al. | 2003/0130665 A1 | 7/2003 | Pinczewski et al. |
| 7,184,814 B2 | 2/2007 | Lang et al. | 2003/0158606 A1 | 8/2003 | Coon et al. |
| 7,198,628 B2 | 4/2007 | Ondrla et al. | 2003/0171757 A1 | 9/2003 | Coon et al. |
| 7,218,232 B2 | 5/2007 | DiSilvestro et al. | 2003/0212403 A1 | 11/2003 | Swanson |
| 7,239,908 B1 | 7/2007 | Alexander et al. | 2003/0216669 A1 | 11/2003 | Lang et al. |
| 7,241,315 B2 | 7/2007 | Evans | 2003/0216741 A1 | 11/2003 | Sanford et al. |
| 7,255,702 B2 | 8/2007 | Serra et al. | 2003/0220641 A1 | 11/2003 | Thelen et al. |
| 7,258,701 B2 | 8/2007 | Aram et al. | 2003/0225413 A1 | 12/2003 | Sanford et al. |
| 7,261,719 B1 | 8/2007 | Twomey et al. | 2004/0018144 A1 | 1/2004 | Briscoe |
| 7,275,218 B2 | 9/2007 | Petrella et al. | 2004/0039395 A1 | 2/2004 | Coon et al. |
| 7,282,054 B2 | 10/2007 | Steffensmeier et al. | 2004/0054372 A1 | 3/2004 | Corden et al. |
| 7,294,133 B2 | 11/2007 | Zink et al. | 2004/0068187 A1 | 4/2004 | Krause et al. |
| 7,297,164 B2 | 11/2007 | Johnson et al. | 2004/0092932 A1 | 5/2004 | Aubin et al. |
| 7,309,339 B2 | 12/2007 | Cusick et al. | 2004/0098133 A1 | 5/2004 | Carignan et al. |
| 7,333,013 B2 | 2/2008 | Berger | 2004/0102785 A1 | 5/2004 | Hodorek et al. |
| 7,335,231 B2 | 2/2008 | McLean | 2004/0102852 A1 | 5/2004 | Johnson et al. |
| 7,371,260 B2 | 5/2008 | Malinin | 2004/0102866 A1 | 5/2004 | Harris et al. |
| 7,383,164 B2 | 6/2008 | Aram et al. | 2004/0106926 A1 | 6/2004 | Leitner et al. |
| 7,385,498 B2 | 6/2008 | Dobosz | 2004/0115586 A1 | 6/2004 | Andreiko et al. |
| 7,388,972 B2 | 6/2008 | Kitson | 2004/0122439 A1 | 6/2004 | Dwyer et al. |
| 7,392,076 B2 | 6/2008 | Moctezuma de La Barrera | 2004/0128026 A1 | 7/2004 | Harris et al. |
| 7,427,272 B2 | 9/2008 | Richard et al. | 2004/0133276 A1 | 7/2004 | Lang et al. |
| 7,468,075 B2 | 12/2008 | Lang et al. | 2004/0138670 A1 | 7/2004 | Metzger |
| 7,474,223 B2 | 1/2009 | Nycz et al. | 2004/0138754 A1 | 7/2004 | Lang et al. |
| 7,488,324 B1 | 2/2009 | Metzger et al. | 2004/0143336 A1 | 7/2004 | Burkinshaw |
| 7,527,631 B2 | 5/2009 | Maroney et al. | 2004/0147927 A1 | 7/2004 | Tsougarakis et al. |
| 7,534,263 B2 | 5/2009 | Burdulis, Jr. et al. | 2004/0153079 A1 | 8/2004 | Tsougarakis et al. |
| 7,542,791 B2 | 6/2009 | Mire et al. | 2004/0158254 A1 | 8/2004 | Eisermann |
| 7,559,931 B2 | 7/2009 | Stone | 2004/0162619 A1 | 8/2004 | Blaylock et al. |
| 7,575,602 B2 | 8/2009 | Amirouche et al. | 2004/0167390 A1 | 8/2004 | Alexander et al. |
| 7,578,851 B2 | 8/2009 | Dong et al. | 2004/0171924 A1 | 9/2004 | Mire et al. |
| 7,582,091 B2 | 9/2009 | Duncan et al. | 2004/0172137 A1 | 9/2004 | Blaylock et al. |

| | | | | | | |
|---|---|---|---|---|---|---|
| 2004/0181144 | A1 | 9/2004 | Cinquin et al. | 2006/0287733 | A1 | 12/2006 | Bonutti |
| 2004/0204644 | A1 | 10/2004 | Tsougarakis et al. | 2007/0015995 | A1 | 1/2007 | Lang et al. |
| 2004/0204760 | A1 | 10/2004 | Fitz et al. | 2007/0016209 | A1 | 1/2007 | Ammann et al. |
| 2004/0212586 | A1 | 10/2004 | Denny | 2007/0027680 | A1 | 2/2007 | Ashley et al. |
| 2004/0220583 | A1 | 11/2004 | Pieczynski et al. | 2007/0066917 | A1 | 3/2007 | Hodorek et al. |
| 2004/0236424 | A1 | 11/2004 | Berez et al. | 2007/0073137 | A1 | 3/2007 | Schoenefeld |
| 2004/0243481 | A1 | 12/2004 | Bradbury et al. | 2007/0083209 | A1 | 4/2007 | Schenberger et al. |
| 2004/0254584 | A1 | 12/2004 | Sarin et al. | 2007/0083214 | A1 | 4/2007 | Duncan et al. |
| 2005/0008887 | A1 | 1/2005 | Haymann et al. | 2007/0083266 | A1 | 4/2007 | Lang |
| 2005/0010300 | A1 | 1/2005 | Disilvestro et al. | 2007/0100258 | A1 | 5/2007 | Shoham et al. |
| 2005/0015022 | A1 | 1/2005 | Richard et al. | 2007/0100462 | A1 | 5/2007 | Lang et al. |
| 2005/0019664 | A1 | 1/2005 | Matsumoto | 2007/0118055 | A1 | 5/2007 | McCombs |
| 2005/0027303 | A1 | 2/2005 | Lionberger et al. | 2007/0118243 | A1 | 5/2007 | Schroeder et al. |
| 2005/0027361 | A1 | 2/2005 | Reiley | 2007/0150068 | A1 | 6/2007 | Dong et al. |
| 2005/0043837 | A1 | 2/2005 | Rubbert et al. | 2007/0156066 | A1 | 7/2007 | McGinley et al. |
| 2005/0049524 | A1 | 3/2005 | Lefevre et al. | 2007/0156171 | A1 | 7/2007 | Lang et al. |
| 2005/0049603 | A1 | 3/2005 | Calton et al. | 2007/0162039 | A1 | 7/2007 | Wozencroft |
| 2005/0059873 | A1 | 3/2005 | Glozman et al. | 2007/0173946 | A1 | 7/2007 | Bonutti |
| 2005/0060040 | A1 | 3/2005 | Auxepaules et al. | 2007/0185498 | A2 | 8/2007 | Lavallee |
| 2005/0065628 | A1 | 3/2005 | Roose | 2007/0191962 | A1 | 8/2007 | Jones et al. |
| 2005/0070897 | A1 | 3/2005 | Petersen | 2007/0198022 | A1 | 8/2007 | Lang et al. |
| 2005/0071015 | A1 | 3/2005 | Sekel | 2007/0203430 | A1 | 8/2007 | Lang et al. |
| 2005/0075641 | A1 | 4/2005 | Singhatat et al. | 2007/0203605 | A1 | 8/2007 | Melton et al. |
| 2005/0096535 | A1 | 5/2005 | de la Barrera | 2007/0219639 | A1 | 9/2007 | Otto et al. |
| 2005/0113840 | A1 | 5/2005 | Metzger et al. | 2007/0219640 | A1 | 9/2007 | Steinberg |
| 2005/0113841 | A1 | 5/2005 | Sheldon et al. | 2007/0224238 | A1 | 9/2007 | Mansmann et al. |
| 2005/0113846 | A1 | 5/2005 | Carson | 2007/0225719 | A1 | 9/2007 | Stone et al. |
| 2005/0119664 | A1 | 6/2005 | Carignan et al. | 2007/0226986 | A1 | 10/2007 | Park et al. |
| 2005/0131662 | A1 | 6/2005 | Ascenzi et al. | 2007/0233121 | A1 | 10/2007 | Carson et al. |
| 2005/0137708 | A1 | 6/2005 | Clark | 2007/0233136 | A1 | 10/2007 | Wozencroft |
| 2005/0148843 | A1 | 7/2005 | Roose | 2007/0233140 | A1 | 10/2007 | Metzger et al. |
| 2005/0149042 | A1 | 7/2005 | Metzger | 2007/0233141 | A1 | 10/2007 | Park et al. |
| 2005/0171545 | A1 | 8/2005 | Walsh et al. | 2007/0233269 | A1 | 10/2007 | Steines et al. |
| 2005/0177170 | A1 | 8/2005 | Fisher et al. | 2007/0233272 | A1 | 10/2007 | Boyce et al. |
| 2005/0203536 | A1 | 9/2005 | Laffargue et al. | 2007/0238069 | A1 | 10/2007 | Lovald et al. |
| 2005/0203540 | A1 | 9/2005 | Broyles | 2007/0239282 | A1 | 10/2007 | Caylor et al. |
| 2005/0216305 | A1 | 9/2005 | Funderud | 2007/0239481 | A1 | 10/2007 | DiSilvestro et al. |
| 2005/0222573 | A1 | 10/2005 | Branch et al. | 2007/0250169 | A1 | 10/2007 | Lang |
| 2005/0234461 | A1 | 10/2005 | Burdulis et al. | 2007/0253617 | A1 | 11/2007 | Arata et al. |
| 2005/0234468 | A1 | 10/2005 | Carson | 2007/0255288 | A1 | 11/2007 | Mahfouz et al. |
| 2005/0244239 | A1 | 11/2005 | Shimp | 2007/0255412 | A1 | 11/2007 | Hajaj et al. |
| 2005/0245934 | A1 | 11/2005 | Tuke et al. | 2007/0262867 | A1 | 11/2007 | Westrick et al. |
| 2005/0245936 | A1 | 11/2005 | Tuke et al. | 2007/0276224 | A1 | 11/2007 | Lang et al. |
| 2005/0267584 | A1 | 12/2005 | Burdulis et al. | 2007/0276400 | A1 | 11/2007 | Moore et al. |
| 2005/0273114 | A1 | 12/2005 | Novak | 2007/0276501 | A1 | 11/2007 | Betz et al. |
| 2005/0283252 | A1 | 12/2005 | Coon et al. | 2007/0282451 | A1 | 12/2007 | Metzger et al. |
| 2005/0283253 | A1 | 12/2005 | Coon et al. | 2007/0288030 | A1 | 12/2007 | Metzger et al. |
| 2006/0004284 | A1 | 1/2006 | Grunschlager et al. | 2008/0009952 | A1 | 1/2008 | Hodge |
| 2006/0015120 | A1 | 1/2006 | Richard et al. | 2008/0015605 | A1 | 1/2008 | Collazo |
| 2006/0030853 | A1 | 2/2006 | Haines | 2008/0021299 | A1 | 1/2008 | Meulink |
| 2006/0038520 | A1 | 2/2006 | Negoro et al. | 2008/0021494 | A1 | 1/2008 | Schmelzeisen-Redeker et al. |
| 2006/0052725 | A1 | 3/2006 | Santilli | 2008/0021567 | A1 | 1/2008 | Meulink et al. |
| 2006/0058803 | A1 | 3/2006 | Cuckler et al. | 2008/0027563 | A1 | 1/2008 | Johnson et al. |
| 2006/0058884 | A1 | 3/2006 | Aram et al. | 2008/0051910 | A1 | 2/2008 | Kammerzell et al. |
| 2006/0058886 | A1 | 3/2006 | Wozencroft | 2008/0058945 | A1 | 3/2008 | Hajaj et al. |
| 2006/0089621 | A1 | 4/2006 | Fard | 2008/0058947 | A1 | 3/2008 | Earl et al. |
| 2006/0093988 | A1 | 5/2006 | Swaelens et al. | 2008/0062183 | A1 | 3/2008 | Swaelens |
| 2006/0094951 | A1 | 5/2006 | Dean et al. | 2008/0065225 | A1 | 3/2008 | Wasielewski et al. |
| 2006/0095049 | A1 | 5/2006 | Zannis et al. | 2008/0112996 | A1 | 5/2008 | Harlow et al. |
| 2006/0100832 | A1 | 5/2006 | Bowman | 2008/0114370 | A1 | 5/2008 | Schoenefeld |
| 2006/0111722 | A1 | 5/2006 | Bouadi | 2008/0133022 | A1 | 6/2008 | Caylor |
| 2006/0122616 | A1 | 6/2006 | Bennett et al. | 2008/0140209 | A1 | 6/2008 | Iannotti et al. |
| 2006/0136058 | A1 | 6/2006 | Pietrzak | 2008/0146969 | A1 | 6/2008 | Kurtz |
| 2006/0142657 | A1 | 6/2006 | Quaid et al. | 2008/0147072 | A1 | 6/2008 | Park et al. |
| 2006/0142774 | A1 | 6/2006 | Metzger | 2008/0161815 | A1 | 7/2008 | Schoenefeld et al. |
| 2006/0142778 | A1 | 6/2006 | Dees | 2008/0172125 | A1 | 7/2008 | Ek |
| 2006/0155380 | A1 | 7/2006 | Clemow et al. | 2008/0195099 | A1 | 8/2008 | Minas |
| 2006/0161167 | A1 | 7/2006 | Myers et al. | 2008/0195107 | A1 | 8/2008 | Cuckler et al. |
| 2006/0172263 | A1 | 8/2006 | Quadling et al. | 2008/0195216 | A1 | 8/2008 | Philipp |
| 2006/0178497 | A1 | 8/2006 | Gevaert et al. | 2008/0200926 | A1 | 8/2008 | Verard et al. |
| 2006/0184177 | A1 | 8/2006 | Echeverri | 2008/0208200 | A1 | 8/2008 | Crofford |
| 2006/0190086 | A1 | 8/2006 | Clemow et al. | 2008/0215059 | A1 | 9/2008 | Carignan et al. |
| 2006/0195198 | A1 | 8/2006 | James | 2008/0230422 | A1 | 9/2008 | Pleil et al. |
| 2006/0204932 | A1 | 9/2006 | Haymann et al. | 2008/0234664 | A1 | 9/2008 | May et al. |
| 2006/0210644 | A1 | 9/2006 | Levin | 2008/0234683 | A1 | 9/2008 | May |
| 2006/0235421 | A1 | 10/2006 | Rosa et al. | 2008/0234685 | A1 | 9/2008 | Gjerde |
| 2006/0271058 | A1 | 11/2006 | Ashton et al. | 2008/0234833 | A1 | 9/2008 | Bandoh et al. |
| 2006/0276796 | A1 | 12/2006 | Creger et al. | 2008/0243127 | A1 | 10/2008 | Lang et al. |
| 2006/0276797 | A1 | 12/2006 | Botimer | 2008/0255674 | A1 | 10/2008 | Rahaman et al. |

| | | |
|---|---|---|
| 2008/0257363 A1 | 10/2008 | Schoenefeld et al. |
| 2008/0262624 A1 | 10/2008 | White et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2008/0294266 A1 | 11/2008 | Steinberg |
| 2008/0300600 A1 | 12/2008 | Guelat et al. |
| 2008/0306558 A1 | 12/2008 | Hakki |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0018666 A1 | 1/2009 | Grundei et al. |
| 2009/0024131 A1 | 1/2009 | Metzger et al. |
| 2009/0043556 A1 | 2/2009 | Axelson et al. |
| 2009/0076371 A1 | 3/2009 | Lang et al. |
| 2009/0076512 A1 | 3/2009 | Ammann et al. |
| 2009/0082770 A1 | 3/2009 | Worner et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0088865 A1 | 4/2009 | Brehm |
| 2009/0088866 A1 | 4/2009 | Case |
| 2009/0089034 A1 | 4/2009 | Penney et al. |
| 2009/0089081 A1 | 4/2009 | Haddad |
| 2009/0093816 A1 | 4/2009 | Roose et al. |
| 2009/0096613 A1 | 4/2009 | Westrick |
| 2009/0099567 A1 | 4/2009 | Zajac |
| 2009/0105837 A1 | 4/2009 | Lafosse et al. |
| 2009/0118736 A1 | 5/2009 | Kreuzer |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1 | 6/2009 | Meridew et al. |
| 2009/0163923 A1 | 6/2009 | Flett et al. |
| 2009/0164024 A1 | 6/2009 | Rudan et al. |
| 2009/0177282 A1 | 7/2009 | Bureau et al. |
| 2009/0187193 A1 | 7/2009 | Maroney et al. |
| 2009/0209884 A1 | 8/2009 | Van Vorhis et al. |
| 2009/0209961 A1 | 8/2009 | Ferrante et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0228016 A1 | 9/2009 | Alvarez et al. |
| 2009/0234360 A1 | 9/2009 | Alexander |
| 2009/0248044 A1 | 10/2009 | Amiot et al. |
| 2009/0254093 A1 | 10/2009 | White et al. |
| 2009/0254367 A1 | 10/2009 | Belcher et al. |
| 2009/0270868 A1 | 10/2009 | Park et al. |
| 2009/0274350 A1 | 11/2009 | Pavlovskaia et al. |
| 2009/0306676 A1 | 12/2009 | Lang et al. |
| 2009/0307893 A1 | 12/2009 | Burdulis, Jr. et al. |
| 2009/0318836 A1 | 12/2009 | Stone et al. |
| 2010/0016984 A1 | 1/2010 | Trabish |
| 2010/0016986 A1 | 1/2010 | Trabish |
| 2010/0023015 A1 | 1/2010 | Park |
| 2010/0030231 A1 | 2/2010 | Revie et al. |
| 2010/0042105 A1 | 2/2010 | Park et al. |
| 2010/0049195 A1 | 2/2010 | Park et al. |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1 | 4/2010 | Keefer |
| 2010/0087829 A1 | 4/2010 | Metzger et al. |
| 2010/0094295 A1 | 4/2010 | Schnieders et al. |
| 2010/0105011 A1 | 4/2010 | Karkar et al. |
| 2010/0121335 A1 | 5/2010 | Penenberg et al. |
| 2010/0137869 A1 | 6/2010 | Borja et al. |
| 2010/0137924 A1 | 6/2010 | Tuke et al. |
| 2010/0145343 A1 | 6/2010 | Johnson et al. |
| 2010/0145344 A1 | 6/2010 | Jordan et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0168857 A1 | 7/2010 | Hatch |
| 2010/0179663 A1 | 7/2010 | Steinberg |
| 2010/0185202 A1 | 7/2010 | Lester et al. |
| 2010/0191244 A1 | 7/2010 | White et al. |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217338 A1 | 8/2010 | Carroll et al. |
| 2010/0228257 A1 | 9/2010 | Bonutti |
| 2010/0249657 A1 | 9/2010 | Nycz et al. |
| 2010/0249796 A1 | 9/2010 | Nycz |
| 2010/0262150 A1 | 10/2010 | Lian |
| 2010/0274253 A1 | 10/2010 | Ure |
| 2010/0281678 A1 | 11/2010 | Burdulis, Jr. et al. |
| 2010/0286700 A1 | 11/2010 | Snider et al. |
| 2010/0292743 A1 | 11/2010 | Singhal et al. |
| 2010/0305574 A1 | 12/2010 | Fitz et al. |
| 2010/0324692 A1 | 12/2010 | Uthgenannt et al. |
| 2011/0004317 A1 | 1/2011 | Hacking et al. |
| 2011/0015636 A1 | 1/2011 | Katrana et al. |
| 2011/0015639 A1 | 1/2011 | Metzger et al. |
| 2011/0029091 A1 | 2/2011 | Bojarski et al. |
| 2011/0029116 A1 | 2/2011 | Jordan et al. |
| 2011/0046735 A1 | 2/2011 | Metzger et al. |
| 2011/0054478 A1 | 3/2011 | Vanasse et al. |
| 2011/0066193 A1 | 3/2011 | Lang et al. |
| 2011/0071528 A1 | 3/2011 | Carson |
| 2011/0071529 A1 | 3/2011 | Carson |
| 2011/0071530 A1 | 3/2011 | Carson |
| 2011/0071532 A1 | 3/2011 | Carson |
| 2011/0071533 A1 | 3/2011 | Metzger et al. |
| 2011/0092804 A1 | 4/2011 | Schoenefeld et al. |
| 2011/0093086 A1 | 4/2011 | Witt et al. |
| 2011/0151027 A1 | 6/2011 | Clineff et al. |
| 2011/0151259 A1 | 6/2011 | Jarman-Smith et al. |
| 2011/0153025 A1 | 6/2011 | McMinn |
| 2011/0190901 A1 | 8/2011 | Weissberg et al. |

FOREIGN PATENT DOCUMENTS

| | | | |
|---|---|---|---|
| CA | 2501041 | A1 | 4/2004 |
| CA | 2505371 | A1 | 5/2004 |
| CA | 2505419 | A1 | 6/2004 |
| CA | 2506849 | A1 | 6/2004 |
| CA | 2546958 | A1 | 6/2005 |
| CA | 2546965 | A1 | 6/2005 |
| CA | 2588907 | A1 | 6/2006 |
| CA | 2590534 | A1 | 6/2006 |
| CH | 117960 | | 5/1927 |
| CN | 1630495 | A | 6/2005 |
| CN | 1728976 | A | 2/2006 |
| CN | 1729483 | A | 2/2006 |
| CN | 1729484 | A | 2/2006 |
| CN | 1913844 | A | 2/2007 |
| CN | 101111197 | A | 1/2008 |
| DE | 337437 | | 5/1921 |
| DE | 3447365 | A1 | 7/1986 |
| DE | 04219939 | A1 | 12/1993 |
| DE | 4421153 | A1 | 12/1995 |
| EP | 0114505 | A1 | 8/1984 |
| EP | 0326768 | A2 | 8/1989 |
| EP | 0579868 | A2 | 1/1994 |
| EP | 0645984 | A1 | 4/1995 |
| EP | 0650706 | A1 | 5/1995 |
| EP | 0916324 | A2 | 5/1999 |
| EP | 1321107 | A1 | 6/2003 |
| EP | 1437102 | A1 | 7/2004 |
| EP | 01486900 | A1 | 12/2004 |
| FR | 1111677 | | 3/1956 |
| FR | 2659226 | A1 | 9/1991 |

| | | | |
|---|---|---|---|
| FR | 2721195 A1 | 12/1995 |
| FR | 2768916 A1 | 4/1999 |
| GB | 2094590 A | 9/1982 |
| GB | 2197790 A | 6/1988 |
| GB | 2442441 A | 4/2008 |
| JP | 59157715 A | 9/1984 |
| JP | 60231208 A | 11/1985 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| TW | 231755 | 5/2005 |
| WO | WO-8909028 A1 | 10/1989 |
| WO | WO-9107139 A1 | 5/1991 |
| WO | WO-9325157 A1 | 12/1993 |
| WO | WO-9528688 A1 | 10/1995 |
| WO | WO-9607361 | 3/1996 |
| WO | WO-9729703 | 8/1997 |
| WO | WO-9952473 A1 | 10/1999 |
| WO | WO-9959106 A1 | 11/1999 |
| WO | WO-0170142 A1 | 9/2001 |
| WO | WO-0184479 A1 | 11/2001 |
| WO | WO-0226145 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A1 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051239 A1 | 6/2005 |
| WO | WO-2005051240 A1 | 6/2005 |
| WO | WO-2005077039 A2 | 8/2005 |
| WO | WO-2006058057 A2 | 6/2006 |
| WO | WO-2006060795 A1 | 6/2006 |
| WO | WO-2006092600 A1 | 9/2006 |
| WO | WO-2006127486 A2 | 11/2006 |
| WO | WO-2006134345 A1 | 12/2006 |
| WO | WO-2007041375 A2 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |
| WO | WO-2007145937 A2 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008101090 A2 | 8/2008 |
| WO | WO-2008112996 A1 | 9/2008 |
| WO | WO-2008140748 A1 | 11/2008 |
| WO | WO-2009001083 A1 | 12/2008 |
| WO | WO-2009025783 A1 | 2/2009 |

OTHER PUBLICATIONS

"AGC Distal Fem Cutter for Dr. Hardy," Biomet, Inc., Jun. 22, 1989.
"AGC Total Knee System, Intramedullary Without Distractor Surgical Technique," 1989, Biomet, Inc.
"AGC Traditional Surgical Overview", copyright 2001 Biomet Orthopedics, Inc.
"AGC-S Total Knee System, Surgical Technique for the AGC-S Total Knee System," 1992, Biomet, Inc.
"Anatomic Axial Alignment Instrumentation," 1994, Biomet, Inc.
"Hand Instruments", High Performance, Precision Series brochure by Arthrotek, copyright 2000.
"M/G Unicompartmental Minimally Invasive Solution Technique—Instrumentation" brochure (2001) Zimmer, Inc., 4 pages.
"The AGC Revision Knee System Surgical Technique," 1997 Biomet, Inc.
"Zimmer® MIS Multi-Reference® 4-in-1 Femoral Instrumentation Surgical Technique, For NexGen® Cruciate Retaining & NexGen Posterior Stablized Kness," brochure (2003; 2008; 2009) 48 pages.
"Zimmer® MOST Options® System Surgical Technique," brochure (2005) Zimmer, Inc., 84 pages.
"Zimmer® NexGen® Complete Knee Solution Extramedullary/Intramedullary Tibial Resector Surgical Technique," brochure (2000; 2002; 2008) 28 pages.
AGC Total Knee System, Unicondylar Surgical Overview, Biomet, Inc. (Jan. 31, 1989) 4 pages.
Genus, brochure entitled "Uni Knee System," Biomet, Inc., Nov. 15, 1998.
Insall/Burstein II Modular Knee System by Zimmer, Inc. copyright 1989.
International Search Report and Written Opinion for PCT/US2009/056670 mailed Mar. 2, 2010 claiming benefit of U.S. Appl. No. 12/211,407, filed Sep. 16, 2008 (which is a CIP of U.S. Appl. No. 12/039,849, filed Feb. 29, 2008, which is a CIP of U.S. Appl. No. 11/971,390, filed Jan. 9, 2008, which is a CIP of U.S. Appl. No. 11/756,957, filed May 31, 2007).
International Search Report and Written Opinion mailed Apr. 22, 2010 for PCT/US2010/024579 claiming benefit of U.S. Appl. No. 12/389,930, filed Feb. 20, 2009.
International Search Report and Written Opinion mailed Jun. 4, 2010 for PCT/US2010/024073 filed Feb. 12, 2010, claiming benefit of U.S. Appl. No. 12/371,096, filed Feb. 13, 2009.
Keys, Graham W., "Reduced Invasive Approach for Oxford II Medial Unicompartmental Knee Replacement—a Preliminary Study," The Knee, (1999) pp. 193-196.
Lombardi, Adolph, et al., "Patient-Specific Approach in Total Knee Arthroplasty," Knee Orthopedics, ORTHOSuperSite (Sep. 1, 2008), 5 pages, http://www.orthosupersite.com/view.aspx?rid=31419, printed May 20, 2010.
Microplasty™ minimally invasive knee instruments brochure, Surgical Technique for the Maxim®, Ascent™ and Vanguard™ Total Knee Systems, Biomet Orthopedics, Inc., Feb. 29, 2004.
MIS Minimally Invasive Solution—The M/G Unicompartmental Knee by Zimmer, [1999] 4 sheets.
MIS Minimally Invasive Solution the M/G Unicompartmental Knee Minimally Invasive Surgical Technique, by Zimmer, copyright 2000 (pp. 1-27).
Nex Gen Complete Knee Solution-Intramedually Instrumentation Surgical Technique-For the NexGen Cruciate Retaining & Legacy Posterior Stablized Knee-Publication (1995; 1999; 2000) pp. 1-33.
NexGen Complete Knee Solution-Multi-Reference 4-in-1 Femoral Instrumentation-Anterior Reference Surgical Technique-Publication [undated] pp. 1-15.
NexGen Complete Knee Solution-Surgical Technique for the LPS-Flex Fixed Bearing Knee-Publication (2000) pp. 1-9.
NexGen System Complete Knee Solution—Design Rationale, 26 pages [undated].
NexGen® Complete Knee Solution-Extramedullary/Intramedullary Tibial Resector Surgical Technique-Publication (undated) pp. 1-22.
Orthopaedic Update, No. 18, The Fudger™—The Ultimate Weapon in the Femoral Referencing War, Biomet, Inc. (2 pages).
Scorpio! Single Axis Total Knee System—Passport Total Knee Instruments—Passport A.R. Surgical Technique by Sryker Howmedica Osteonics, Copyright 2000.
Simple Instruments Surgical Technique for the Knee, copyright 2000 Biomet, Inc.
Surgical Navigation for Total Knee Arthroplasty-Believed to have been presented at the American Academy of Orthopedic Surgeons in Feb. 2001.
The Oxford, brochure entitled "Unicompartmental Knee System", Biomet Orthopedics, Inc., Jul. 15, 2004.
"Patient Matched PMI Implants, C.A.M.R.A. 3-D Imaging," brochure, Biomet, Inc. (1990) 6 pages.
Birnbaum, Klaus, M.D., "Computer-Assisted Orthopedic Surgery With Individual Templates and Comparison to Conventional Method," SPINE vol. 26, No. 4, pp. 365-370 (2001) Lippincott Williams & Wilkins, Inc.
Botha, Charl P., Technical Report: DeVIDE—The Delft Visualisation and Image processing Development Environment, pp. 1-49 (May 31, 2006).

Eckhoff, Donald G., et al., "Three-Dimensional Mechanics, Kinematics, and Morphology of the Knee Viewed in Virtual Reality," The Journal of Bone & Joint Surgery, vol. 81 (Dec. 4, 2005) pp. 71-80.

Fortin, Thomas, D.D.S., Ph.D., et al., "Precise Dental Implant Placement in Bone Using Surgical Guides in Conjunction with Medical Imaging Techniques," Journal of Oral Implantology, Clinical, vol. 26, No. 4 (2000) pp. 300-303.

Haaker, R.G., et al., "Minimal-invasive navigiert implantierte unikondyläre Knieendoprothese," Orthopäde 2006 35:1073-1079 (2006) Spinger Medizin Verlag.

Hafez, M.A., et al., "Computer-assisted Total Knee Arthroplasty Using Patient-specific Templating," Clinical Orthopaedics and Related Research, No. 444 (pp. 184-192) 2006 Lippincott Williams & Wilkins.

Hazan, Eric J., M.D., "Computer-Assisted Orthopaedic Sugery, A New Paradigm," Techniques in Orthopaedics® vol. 18, No. 2, (2003) pp. 221-229.

Hutmacher, Dietmar, W., "Scaffolds in tissue engineering bone and cartilage," Biomaterials, 2000 Elsevier Science Ltd. (pp. 2529-2543).

International Preliminary Report on Patentability for PCT/US2007/013223 issued Nov. 26, 2007.

International Search Report and Written Opinion for PCT/US2007/013223 mailed Nov. 26, 2007.

International Search Report and Written Opinion for PCT/US2009/039507 mailed Jul. 14, 2009.

International Search Report and Written Opinion for PCT/US2009/039578 mailed Jul. 31, 2009.

Invitation to Pay Additional Fees with Partial International Search mailed Nov. 26, 2009 for PCT/US2009/056670.

Kaus, Michael R., Ph.D., "Automated Segmentation of MR Images of Brain Tumors," Radiology, vol. 218, No. 2, (2001) pp. 586-591.

Klein, M., "Robot assisted insertion of craniofacial implants—clinical experience," CARS 2001, pp. 133-138 (2001) Elsevier Science B.V.

Lynch, John A., et al., "Cartilage segmentation of 3D MRI scans of the osteoarthritic knee combining user knowledge and active contours," Medical Imaging 2000: Image Processing SPIE vol. 3979 (2000) pp. 925-935.

Nicholls, Paul, M.D., "Trauma Grand Rounds PMI (Patient-Matched Implants)" brochure, Biomet Orthopedics, Inc., (Feb. 29, 2000) 1 page.

Overhoff, H.M., et al., "Total Knee Arthroplasty: Coordinate System Definition and Planning based on 3-D Ultrasound Image Volumes," CARS 2001, pp. 283-288, (2001) Elsevier Science B.V.

Portheine, F., "CT-basierte Planung und DISOS-Schablonennavigation in der Kniegelenkendoprothetik," in Navigation und Robotic in der Gelenk—und Wirbelsäulenchirugie, Kapitel 32, Springer Verlag (2003) pp. 262-269.

Portheine, F., et al., Entwicklung eines klinischen Demonstrators für die computerunterstützte Orthopädische Chirurgie mit CT-Bildbasierten Individualschablonen, Bildverarbeitung fur die Medizin (1998) 5 pages.

Portheine, K., "Development of a clinical demonstrator for computer assisted orthopedic surgery with CT-image based individual templates," Computer Assisted Radiology and Surgery, pp. 944-949, (1997) Elsevier Science B.V.

Radermacher, "Computer Assisted Orthopaedic Surgery with Image Based Individual Templates," Clinical Orthopaedics and Related Research No. 354, pp. 28-38 (1998) Lippincott Williams & Wilkins.

Radermacher, K., et al., "Computer Integrated Orthopaedic Surgery: Connection of Planning and Execution in Surgical Intervention," Computer-integrated surgery: technology and clinical applications, (1996) pp. 451-463.

Radermacher, K., et al., "CT Image-Based Planning and Execution of Interventions in Orthopedic Surgery Using Individual Templates, Experimental Results and Aspects of Clinical Applications," Computer Assisted Orthopedic Surgery (CAOS), pp. 42-52, (1995) Hogrefe & Huber Publishers.

Radermacher, K., et al., "Image Guided Orthopedic Surgery Using Individual Templates," Springer Berlin/Heidelberg, CVRMed-MRCAS'97, vol. 1205/1997 pp. 606-615).

Radermacher, K., et al., "Technique for Better Execution of CT Scan Planned Orthopedic Surgery on Bone Structures," Supplied by the British Library—"The world's knowledge" 2nd Congress of ISCAS Conference in Berlin Germany (Jun. 1995) pp. 933-938.

Schuller-Götzburg, P., et al., 3D-Implantatplanung und Stereolithographie-Implantatbohrschablonen, Stomatologie 101.3, pp. 55-59 (2004).

Sharp, S. Michael, Ph.D., Patient-Specific, Resurfacing Bi-Compartmental Arthuroplasty, Futuretech, Orthopaedic Product News (Mar./Apr. 2008) pp. 12-15.

Sisto, Domenick, J., et al., "Custom Patellofemoral Arthroplasty of the Knee Surgical Technique," Journal of Bone and Joint Surgery, vol. 89-A, pp. 214-225 (2007).

Slammin, John et al, "Do You Have This Implant in My Size?", MDT Medical Design Technology, 3 pages, http://www.mdtmag.com/scripts/ShowPR.asp?PUBCODE=046&ACCT=0007796&ISSUE... accessed Jul. 31, 2008.

Steinwachs, Matthias Reinhard, "Cartilage Repair—Autologous Chondrocyte Transplantation and Autologous Matrix-induced Chondrogenesis," European Musculoskeletal Review (2006) pp. 65-68.

"Amazing Precision. Beautiful Results. The next evolution of MAKOplasty® is here," brochure. (Feb. 2009) MAKO Surgical Corp. 6 pages.

"Ascent Total Knee System," brochure. Biomet, Inc. (1999) 16 sheets.

"Customized Patient Instruments, Patient specific instruments for patient specific needs," brochure. (2008) DePuy Orthopaedics, Inc. 14 sheets.

"Customized Patient Instruments, Primary Cruciate Retaining Surgical Technique for use with the Sigma® Knee System Utilizing Specialist® 2 Instrumentation," brochure. (2008) DePuy Orthopaedics, Inc. pp. 1-23.

"Discovery® Elbow System Surgical Technique," brochure. Biomet Orthopedics, Inc. (2008) pp. 1-25.

"Discovery® Elbow System," brochure. Biomet Orthopedics, Inc. (2007) 3 sheets.

"Hipsextant Instructions of Use." (2011) Surgical Planning Associates, Inc. 19 pages.

"Knee tensor combined with laser femoral head locator," Research Disclosure. Jul. 2006. No. 507; p. 903.

"Method for constructing an allograft sleeve." Research Disclosure (Dec. 2003) No. 476, p. 1294.

"OSS™ Orthopaedic Salvage System, Femoral/Tibial Augmentation," brochure. Biomet Orthopedics, Inc., (2003) pp. 1-8 (12 sheets).

"Regenerex® Tibial Cone Augment, Surgical Technique Addendum to the Vanguard® SSK Revision System," brochure. Biomet® Orthopedics. (2009) pp. 1-8 (12 sheets).

"Signature™ Personalized Patient Care, Surgical Technique Addendum to the Vanguard Knee System" brochure. Biomet® Orthopedics, Inc. (2009) pp. 1-8.

"TruMatch™ Personalized knee replacement solutions," tri-fold brochure. (2009) SIGMA® DePuy Orthopaedics, Inc. 2 pages.

"Vanguard® PFR Partial Knee Patellofemoral Replacement System," Surgical Technique brochure. Biomet Orthopaedics, (2010) pp. 1-25.

"Zimmer® UniSpacer® Knee System," brochure. (2005) Zimmer, Inc. 4 sheets.

Cohen, Zohara A., et al. "Knee cartilage topography, thickness, and contact areas from MRI: in-vitro calibration and in-vivo measurements." Journal of the OsteoArthritis Research Society International. Osteoarthritis and Cartilage, (1999) vol. 7; No. 1 pp. 95-109.

International Preliminary Report on Patentability and Written Opinion for PCT/US2009/039578 mailed Oct. 28, 2010 claiming benefit of U.S. Appl. No. 12/103,834, filed Apr. 16, 2008.

International Preliminary Report on Patentability and Written Opinion mailed Oct. 28, 2010 for PCT/US2009/039507 claiming benefit of U.S. Appl. No. 12/103,824, filed Apr. 16, 2008.

International Preliminary Report on Patentability for PCT/US2007/013223 mailed Dec. 24, 2008 claiming benefit of U.S. Appl. No. 11/756,057, filed May 31, 2007.

International Preliminary Report on Patentability mailed Mar. 31, 2011 for PCT/US2009/056670 claiming benefit of U.S. Appl. No. 12/211,407, filed Sep. 16, 2008.

International Search Report and Written Opinion mailed Aug. 19, 2010 for PCT/US2010/024584 claiming benefit of U.S. Appl. No. 12/389,901, filed Feb. 20, 2009.

International Search Report and Written Opinion mailed Dec. 7, 2010 for PCT/US2010/050701 claiming benefit of U.S. Appl. No. 12/571,969, filed Oct. 1, 2009.

International Search Report and Written Opinion mailed Jun. 10, 2010 for PCT/US2010/038177 claiming benefit of U.S. Appl. No. 12/483,807, filed Jun. 12, 2009.

International Search Report and Written Opinion mailed May 9, 2011 for PCT/US2011/026412 claiming benefit of U.S. Appl. No. 12/872,663, filed Aug. 31, 2010.

International Search Report and Written Opinion mailed Oct. 5, 2010 for PCT/US2010/038845 claiming benefit of U.S. Appl. No. 12/486,992, filed Jun. 18, 2009.

Invitation to Pay Additional Fees mailed May 3, 2011 for PCT/US2011/026333 claiming benefit of U.S. Appl. No. 12/714,023, filed Feb. 26, 2010.

Kelly, Todd C., M.D., "Role of Navigation in Total Hip Arthroplasty." The Journal of Bone & Joint Surgery(2009) pp. 153-158. vol. 91-A, Supplement 1.

Murphy, S.B., et al. "The Hip Sextant; Navigation of Acetabular Component Orientation Using a Mechanical Instrument," brochure. (2009) 1 page.

Radermacher, Klaus, et al. "Computer Assisted Orthopaedic Individual Templates." Clinical Orthopaedics and Related Research. (Sep. 1998) No. 354; pp. 28-38.

International Preliminary Report on Patentability mailed Aug. 25, 2011 for PCT/US2010/024073 filed Feb. 12, 2010, claiming benefit of U.S. Appl. No. 12/371,096, filed Feb. 13, 2009.

International Preliminary Report on Patentability mailed Sep. 1, 2011 for PCT/US2010/024579 claiming benefit of U.S. Appl. No. 12/389,930, filed Feb. 20, 2009.

International Preliminary Report on Patentability mailed Sep. 1, 2011 for PCT/US2010/024584 claiming benefit of U.S. Appl. No. 12/389,901, filed Feb. 20, 2009.

International Search Report and Written Opinion mailed Aug. 9, 2011 for PCT/US2011/026333 claiming benefit of U.S. Appl. No. 12/714,023, filed Feb. 26, 2010.

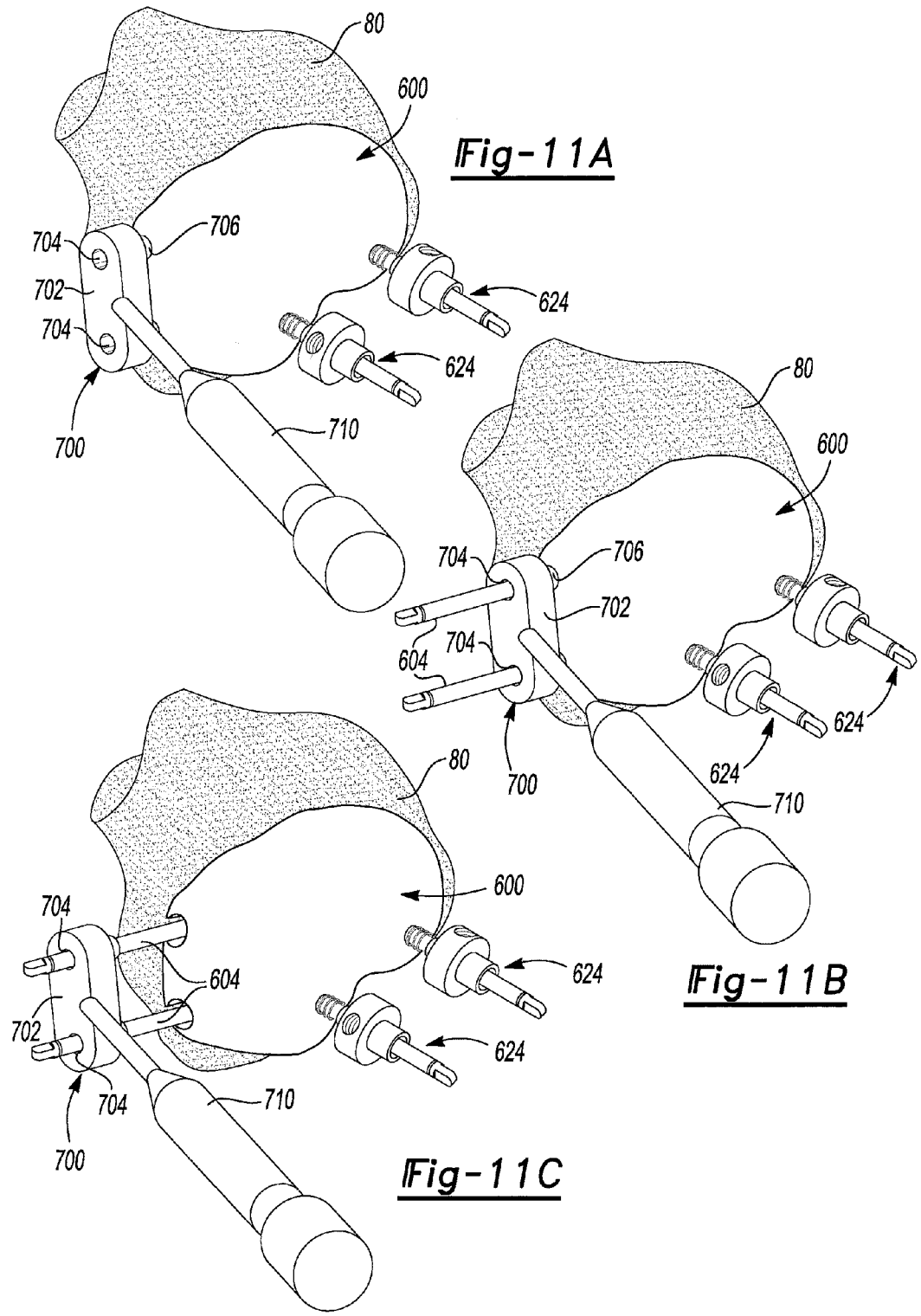

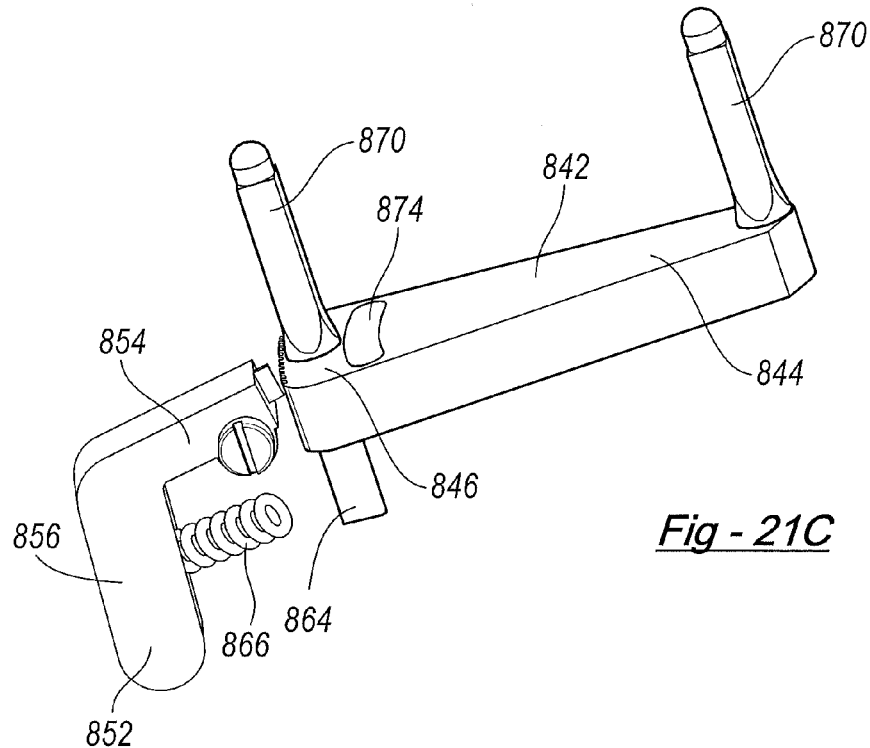
*Fig - 21C*
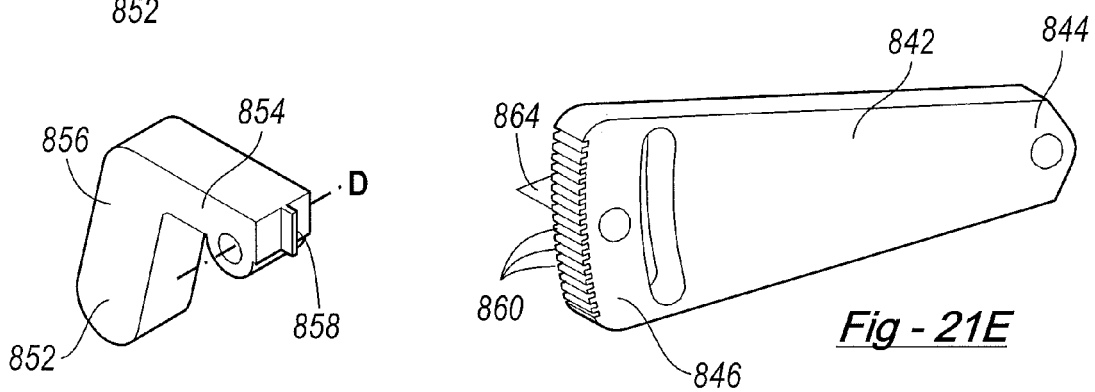
*Fig - 21D*
*Fig - 21E*
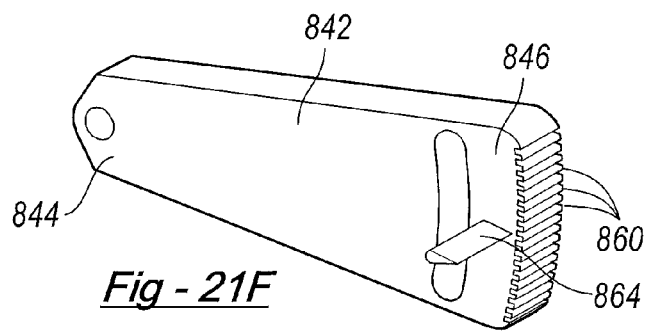
*Fig - 21F*

PATIENT SPECIFIC ALIGNMENT GUIDE AND INTER-OPERATIVE ADJUSTMENT

CROSS-REFERENCE TO RELATED APPLICATIONS

This application is a continuation-in part of U.S. application Ser. No. 11/756,057, filed on May 31, 2007, and published as U.S. Patent Publication No. 2007/0288030 on Dec. 13, 2007, which claims the benefit of U.S. Provisional Application No. 60/812,694, filed on Jun. 9, 2006. This application is also a continuation-in-part of U.S. application Ser. No. 11/363,548, filed on Feb. 27, 2006, now U.S. Pat. No. 7,780,672 issued on Aug. 24, 2010. The disclosures of the above applications are incorporated herein by reference.

INTRODUCTION

Proper alignment of prosthetic components in knee arthroscopy is an important factor in the longevity and function of the implant. Misalignment can cause increased wear of the implant, patient discomfort, and functional limitation.

Although various methods and devices are known for addressing the above problems, patient specific alignment methods and alignment guides are still desirable.

SUMMARY

The present teachings provide a method of preparing a joint for a prosthesis in a patient. In one aspect, the method includes obtaining scan data associated with the joint of the patient, preparing a three-dimensional image of the joint based on the scan data, preparing a pre-operative surgical plan based on the scan data, and preparing an image of a patient-specific alignment guide, and intra-operatively modifying the surgical plan.

In another aspect, the method includes securing a patient-specific alignment guide to a joint surface of the patient, attaching a guide element through the alignment guide to the joint surface, removing the alignment guide without removing the guide element, supporting a cutting block having an adjustable cutting guide on the guide element, adjusting the cutting guide relative to the cutting block, and resecting the joint surface using the guide element.

The present teachings also provide a method of preparing a knee joint for a prosthesis in a patient. The method includes mating a patient-specific femoral alignment guide to a femoral joint surface of the patient, inserting a first guide element through the femoral alignment guide into the anterior or the anterior-medial side of the femoral joint surface, removing the femoral alignment guide without removing the first guide element, supporting an adjustable resection device having a cutting guide on the first guide element, adjusting the orientation of the cutting guide relative to the resection device, and drilling an aperture into the femur joint surface through the resection device. The method further includes inserting a second guide element into the aperture, removing the adjustable resection device, supporting a cutting block on the second guide element, and resecting the femoral joint surface.

Further areas of applicability of the present invention will become apparent from the description provided hereinafter. It should be understood that the description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 11A is a perspective view of the femoral alignment guide of FIG. 8 shown with a drill guide;

FIG. 11B is a perspective view of the femoral alignment guide of FIG. 11A shown with two guide pins drilled through the drill guide;

FIG. 11C is perspective view of the femoral alignment guide of FIG. 11B showing the removal of the drill guide;

FIGS. 21A-F illustrate various perspective views of components of a rotational adjustment mechanism according to the present teachings.

DESCRIPTION OF VARIOUS ASPECTS

The following description is merely exemplary in nature and is in no way intended to limit the scope of the present teachings, applications, or uses. For example, although the present teachings are illustrated for alignment guides in knee surgery, the present teachings can be used for other guides, templates, jigs, drills, rasps or other instruments used in various orthopedic procedures.

The present teachings provide a method for preparing patient-specific alignment guides for use in orthopedic surgery for a joint, such as, for example, the knee joint. Conventional, not patient-specific, prosthesis components available in different sizes can be used with the alignment guides, although patient-specific femoral and tibial prosthesis components prepared with computer-assisted image methods can also be used. Computer modeling for obtaining three dimensional images of the patient's anatomy, such as a patient's joint, for example, the patient-specific prosthesis components, when used, and the alignment guides and templates can be provided by various CAD programs and/or software available from various vendors or developers, such as, for example, from Materialise USA, Ann Arbor, Mich.

Figure 1:
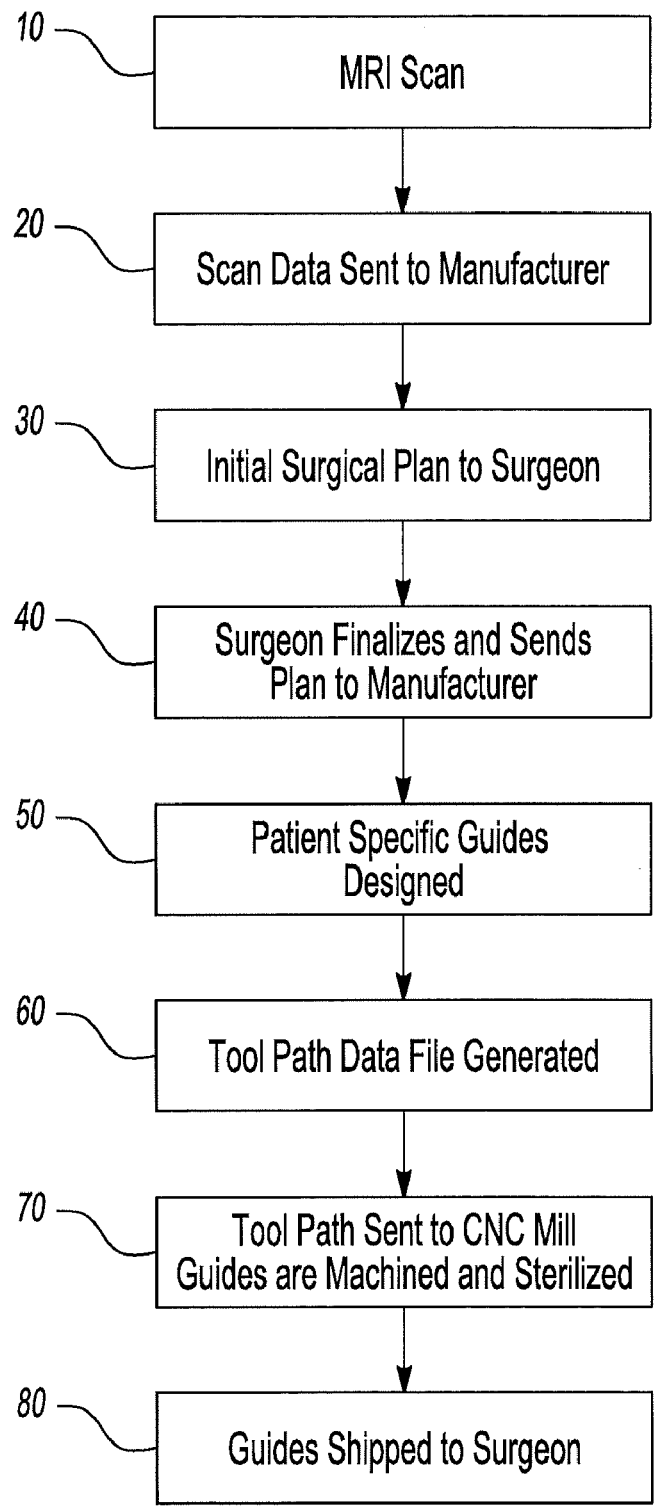
FIG. 1 is a flowchart of an exemplary method of preparing patient specific alignment guides according to the present teachings.
Figure 2:
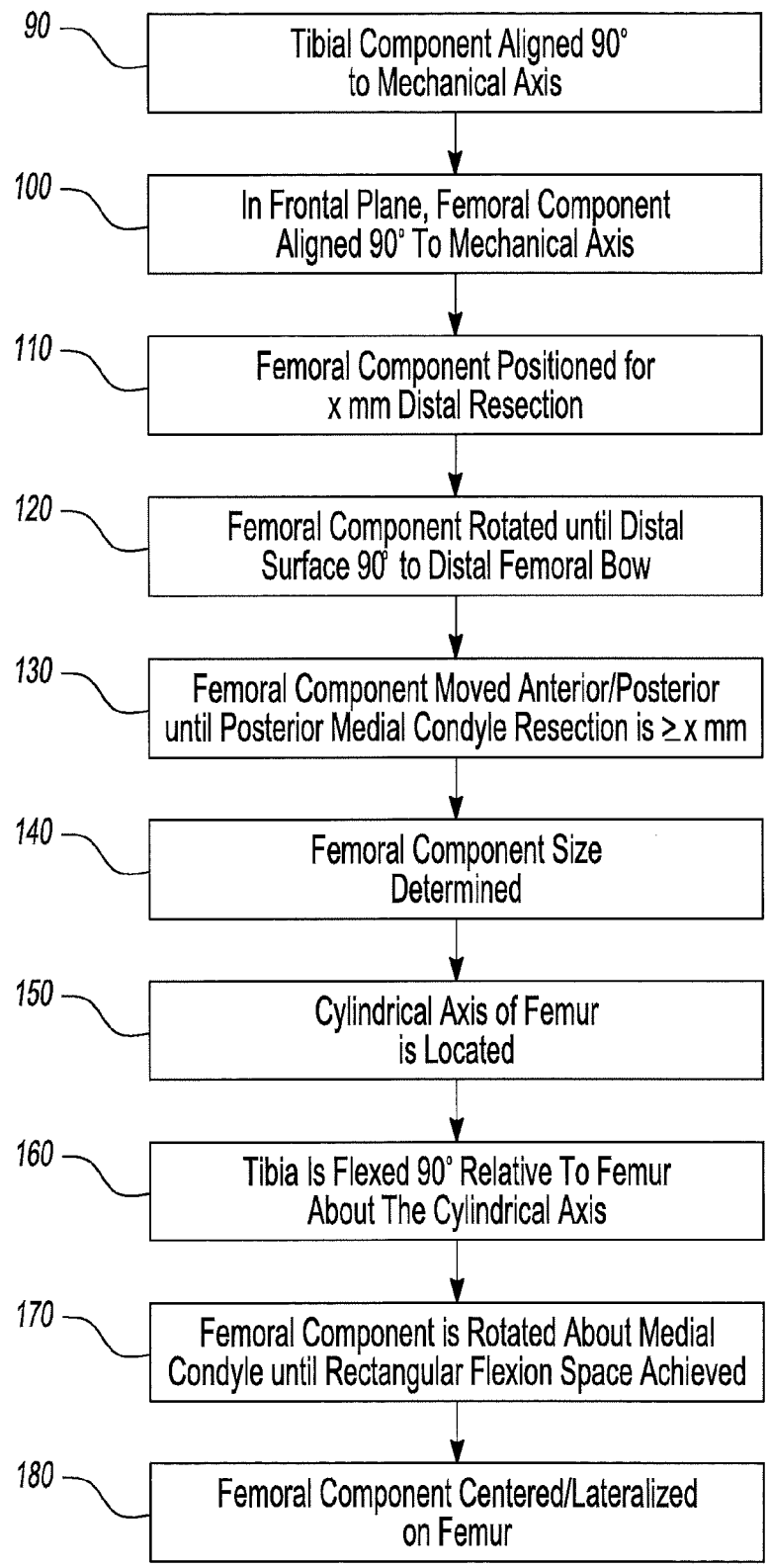
FIG. 2 is a flowchart of an alignment method according to the present teachings.
Figure 3:
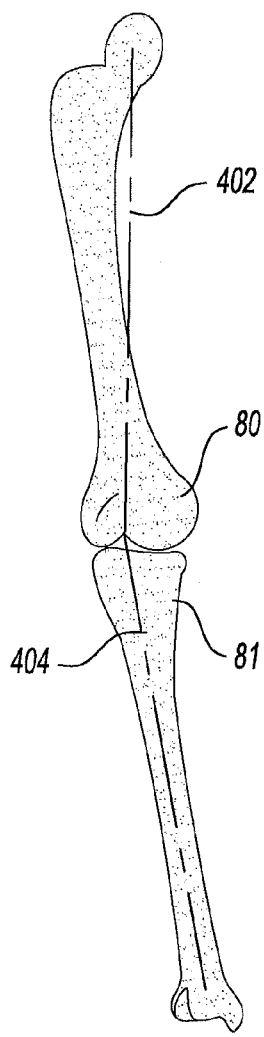
FIG. 3 is a view illustrating the mechanical axis in a patient's anatomic image.

Referring to FIG. 1, an MRI scan or a series of CT scans of the entire leg of the joint to be reconstructed, including hip and ankle, as shown in FIG. 3, can be performed at a medical facility or doctor's office, at aspect 10. In some cases, the scan may be performed with the patient wearing an unloader brace to stress the ligaments. The scan data obtained can be sent to a manufacturer, at aspect 20. The scan data can be used to construct a three-dimensional image of the joint and provide an initial implant fitting and alignment in a computer file form or other computer representation. The initial implant fitting and alignment can be obtained using an alignment method, such as the alignment method illustrated in FIG. 2 and described below. Other alignment methods can also be used, such as alignment protocols used by individual surgeons.

Figure 7:
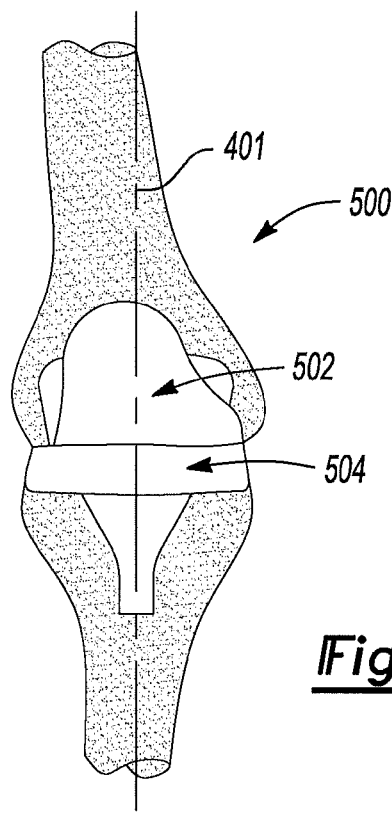
FIG. 7 is an exemplary image of a patient's anatomy with implants shown, as viewed in interactive software according to the present teachings.
Figure 8:
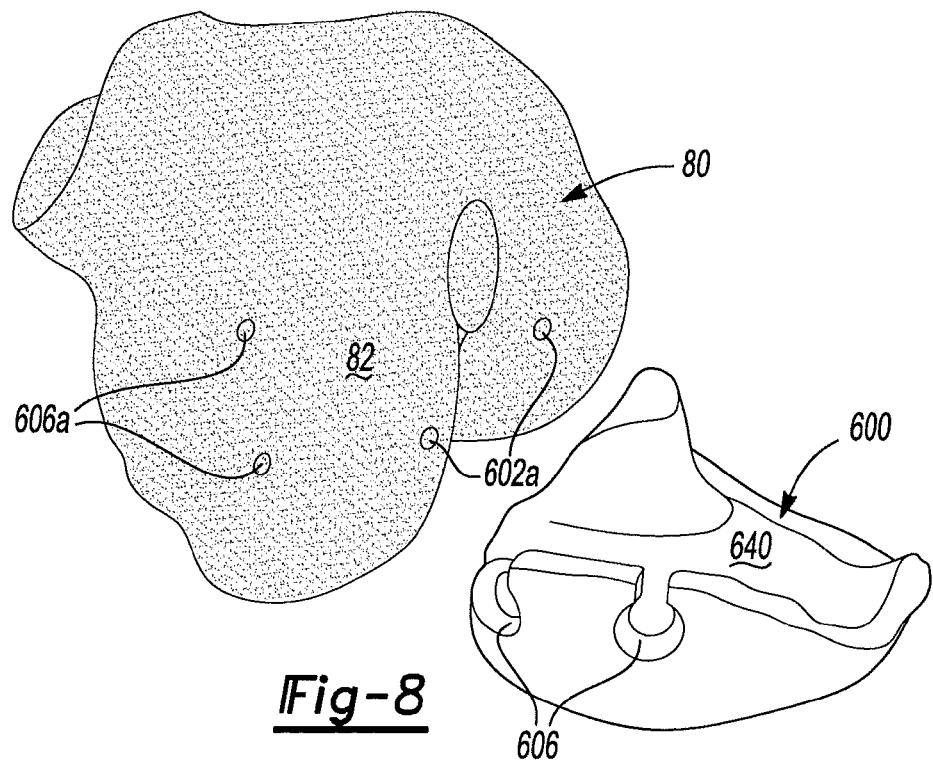
FIG. 8 is a perspective view of an exemplary femoral alignment guide according to the present teachings, shown next to a corresponding anatomic femur.
Figure 9A:
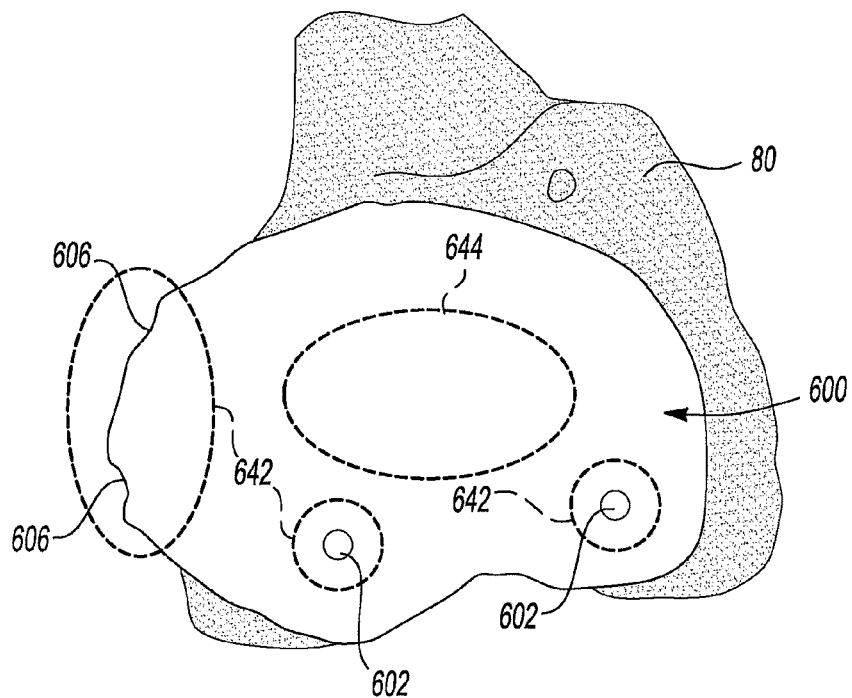
FIGS. 9A and 9B are perspective view of the femoral alignment guide of FIG. 8 shown mounted on the femur.
Figure 9B:
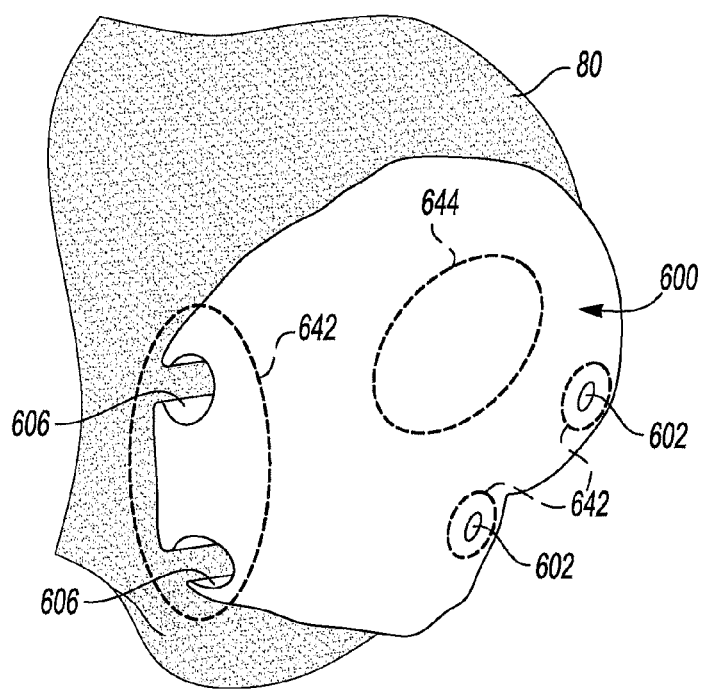

The outcome of the initial fitting is an initial surgical plan that can be printed or provided in electronic form with corresponding viewing software. The initial surgical plan can be surgeon-specific, when using surgeon-specific alignment protocols. The initial surgical plan, in a computer file form associated with interactive software, can be sent to the surgeon, or other medical practitioner, for review, at 30. The surgeon can incrementally manipulate the position of images of implant components 502, 504 in an interactive image form 500 of the joint, as illustrated in FIG. 7. After the surgeon modifies and/or approves the surgical plan, the surgeon can send the final, approved plan to the manufacturer, at 40.

Various methods of sending the initial and final surgeon-approved surgical plans can be used. The surgical plans can be, for example, transferred to an electronic storage medium, such as CD, DVD, flash memory, which can then be mailed using regular posting methods. Alternatively, the surgical plan can be e-mailed in electronic form or transmitted through the internet or other web-based service, without the use of a storage medium.

After the surgical plan is approved by the surgeon, patient-specific alignment guides for the femur and tibia can be developed using a CAD program or other imaging software, such as the software provided by Materialise, for example, according to the surgical plan, at 50. Computer instructions of tool paths for machining the patient-specific alignment guides can be generated and stored in a tool path data file, at 60. The tool path can be provided as input to a CNC mill or other automated machining system, and the alignment guides can be machined from polymer, ceramic, metal or other suitable material, and sterilized, at 70. In one aspect, the patient-specific alignment guides can be manufactured by rapid prototyping methods, including, for example, stereolithography. The sterilized alignment guides can be shipped to the surgeon or medical facility, at 80 for use during the surgical procedure.

Figure 4:
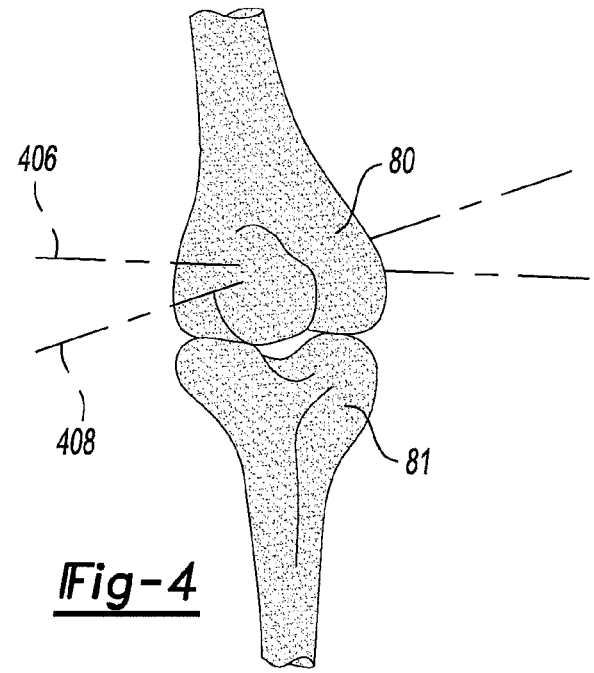
FIG. 4 is a view illustrating the transepicondylar and cylindrical axes in a patient's anatomic image.

Referring to FIG. 2, an exemplary method for providing the initial implant fitting and alignment is illustrated. The method can be modified or completely replaced according to a surgeon-specific alignment protocol. After the scan data is converted to three dimensional images of the patient anatomy from hip to ankle, images of the tibial and femoral components can be manipulated for obtaining patient-specific alignment by making use of the femoral and tibial mechanical axes 402, 404, illustrated in FIG. 3, and the transepicondylar and cylindrical axes 406, 408, illustrated in FIG. 4. Images of the knee joint anatomy can include images of the joint surfaces of the distal femur and proximal tibial with or without the associated soft tissues, such as articular cartilage, on the respective bone surfaces.

Generally, the femoral mechanical axis is defined as the line joining the center of the femoral head and the center of the intercondylar notch. The femoral anatomic axis is defined as the line along the center of the femoral shaft. The tibial mechanical axis is the line joining the center of the tibial plateau to the center of the tibial plafond or the center of the distal end of the tibia. The tibial anatomic axis is the line along the center of the tibial shaft. The transepicondylar axis is the line connecting the most prominent points of the epicondyles. The cylindrical axis is the line connecting the centers of the condyles when the condyles are approximated by coaxial cylinders. A detailed discussion of the various joint-related axes and the relation of the transepicondylar axis 406 and cylindrical axis 408 is provided in Eckhoff et al, *Three-Dimensional Mechanics, Kinematics, and Morphology of the Knee Viewed in Virtual Reality*, J Bone Joint Surg Am. 87:71-80, 2005, which is incorporated herein by reference.

Figure 5:
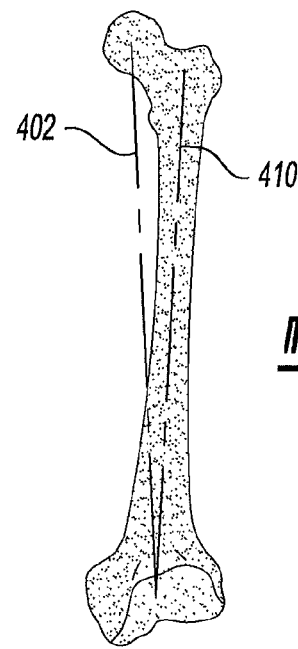
FIG. 5 is a view illustrating the mechanical and anatomic axes in a patient's femoral image.

The relation of the femoral mechanical axis 402 to the anatomic axis 410 for the femur is illustrated in FIG. 5. The femoral and tibial mechanical axes 402, 404 may or may not coincide, as illustrated in FIG. 3. In the following discussion, reference is made to a single mechanical axis 401 encompassing the femoral and tibial mechanical axes 402, 404. The alignment procedure illustrated in FIG. 2 makes use of the mechanical, anatomic, transepicondylar and cylindrical axes in various degrees. The present teachings, however, are not limited to this alignment procedure. Multiple alignment procedures can be provided to accommodate the experience and preference of individual surgeons. For example, the alignment procedure can be based on the anatomic and mechanical axes, or can be substantially based on the cylindrical axis. Further, the alignment procedure can be deformity-specific, such that is adapted, for example, to a valgus or varus deformity.

With continued reference to FIGS. 2-5 and 7, in the image space, the tibial component 504 can be aligned 90° to the mechanical axis 401, at aspect 90. In the frontal plane, the femoral component 502 can be aligned 90° to the mechanical axis 401, at aspect 100. The femoral component 502 can be positioned for "x" mm distal resection, at 110, where "x" can be about 9 mm or other measurement as indicated for a specific patient. The femoral component 502 can be rotated until its distal surfaces are at 90° to the distal femoral bow (component flexion/extension), at 120. The femoral component 502 can be moved anteriorly/posteriorly until the posterior medial condyle resection is greater or equal to "x" mm, at aspect 130.

The femoral component size can be determined by observing the anterior resection relative to anterior cortex, at 140. If the femoral size is adjusted, the new size can be positioned at the same location relative to the distal and posterior cut planes.

The cylindrical axis 408 of the femur can be located, at aspect 150. The tibia can be flexed 90° relative to the femur about the cylindrical axis 408, at aspect 160. The femoral component 502 can be rotated about the medial condyle until a rectangular flexion space is achieved, at aspect 170. Alternatively, the rotation can be relative to the transepicondylar axis, anterior/posterior axis, and posterior condylar axis, or a combination of all four axes. The femoral component 502 can be centered or lateralized on the femur, at aspect 180. The location for various distal holes for locating the femoral resection block can be also determined.

Referring to FIGS. 6, and 8-15B, an exemplary alignment guide 600 and method of use is illustrated in connection with the patient's femur 80. Reference numbers 200-250 relate to aspects of the method of FIG. 6 and are described in connection with the instruments shown in FIGS. 8-15B for the femur 80.

The alignment guide 600 includes an inner guide surface 640 designed to closely conform, mate and match the femoral joint surface 82 of the patient in three-dimensional space such that the alignment guide 600 and the femoral joint surface are in a nesting relationship to one another. Accordingly, the alignment guide 600 can conform, mate and snap on or "lock" onto the distal surface of the femur 80 in a unique position determined in the final surgical plan, at 200. The alignment guide 600 can have variable thickness. In general, the alignment guide 600 can be made as thin as possible while maintaining structural stiffness. For example, certain areas around and adjacent various securing or guiding apertures 602, 606 can be thickened to provide structural support for guiding a drill or for holding a drill guide or supporting other tools or devices. Exemplary thickened areas 642 are indicated with dotted lines in FIGS. 9A and 9B. Other areas can be cut out for viewing the underlying bone or cartilage of femoral joint surface 82. Viewing areas 644 are indicated with dotted lines in FIGS. 9A and 9B.

Figure 10A:
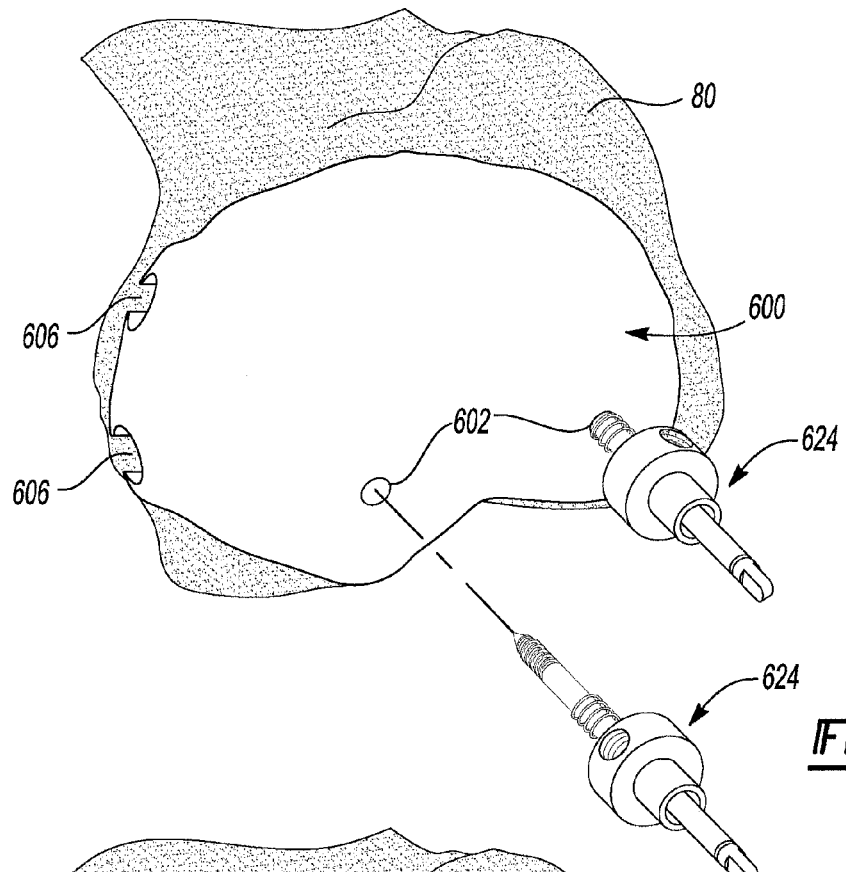
FIGS. 10A and 10B are perspective view of the femoral alignment guide of FIG. 8 shown with spring pins securing the alignment guide to the femur.
Figure 10B:
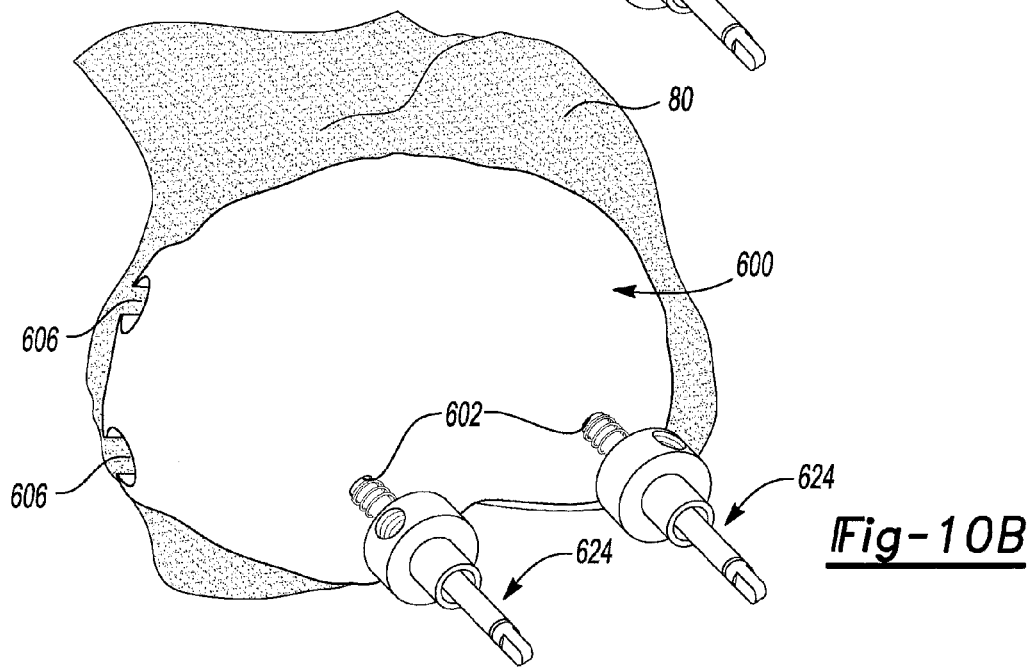
Figure 13A:
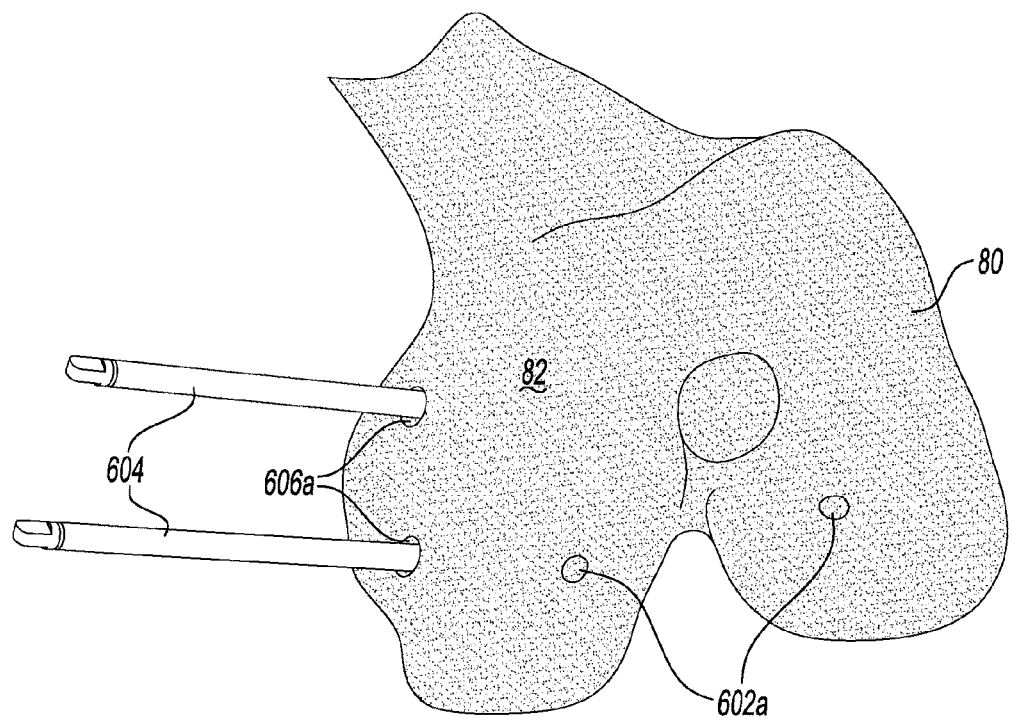
FIG. 13A is a perspective view of FIG. 12B illustrating the guide pins after the removal of the femoral alignment guide.
Figure 13B:
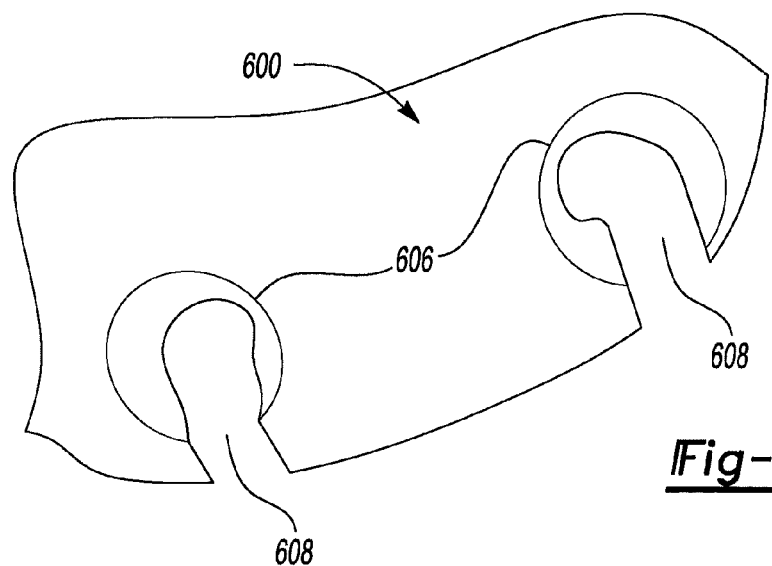
FIG. 13B illustrated a detail of the femoral alignment guide of FIG. 12B.

Referring to FIGS. 10A and 10B, the alignment guide 600 can be secured to the femoral joint surface 82 with fixation members or fasteners 624, such as, for example, spring pins, or other securing fasteners that are received through distal apertures 602 of the alignment guide 600. Locating holes 602a corresponding to the apertures 602 of the alignment guide 600 can be drilled in the distal femur 80 to locate a femoral resection block or other cutting device 620, such as a 4-in-1 cutting block, at 220. The alignment guide 600 can also include guiding apertures 606. Guiding apertures 606 are shown in the anterior-medial side relative to the femur 80, but can also be made in the anterior side of the femur 80 or in other locations and orientations. The guiding apertures 606 can be counter-bored and have a partially open portion 608 in their perimeter for sliding the alignment guide off pins or other fasteners without removing such fasteners, as shown in FIG. 13A and discussed below.

Referring to FIGS. 11A and 11B, a drill guide 700 can be placed in alignment with the guiding apertures 606. The drill guide 700 can include a body 702 having guiding bores 704 corresponding to the guiding apertures 606. The guiding bores 704 can have portions 706 that extend beyond the body 702 and into the guiding apertures 606 for facilitating alignment. The drill guide 700 can also include a handle 710 extending sideways from the body 702 and clear from the drilling path.

Figure 6:
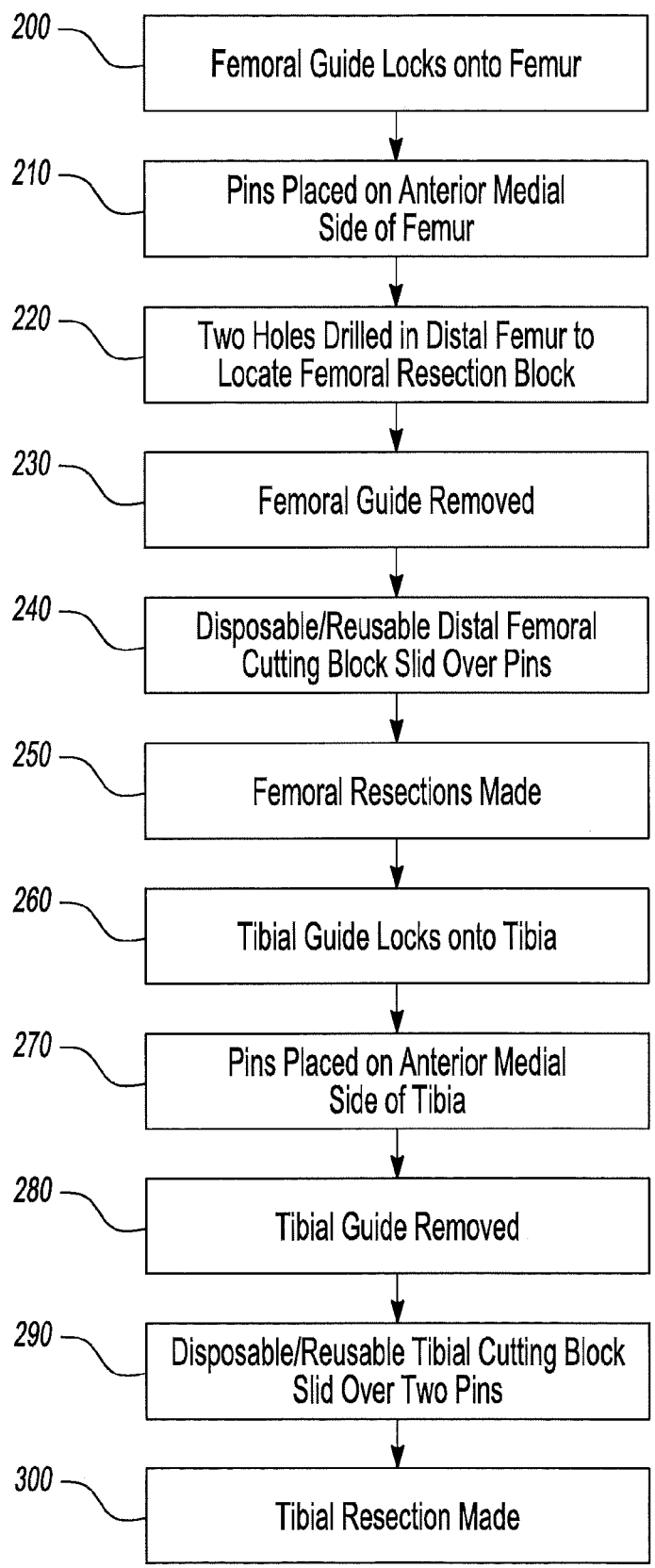
FIG. 6 is a flowchart of an exemplary method of using patient specific alignment guides according to the present teachings.

Referring to FIG. 11C, guide elements 604, such as pins or other fasteners, for example, can be drilled through the guiding bores 704 of the drill guide 700 on the anterior or anterior-medial side of the femur 80, at aspect 210 of the method of FIG. 6. The guide elements 604 can be parallel or at other angles relative to another. The guide elements 604 can define a plane that is parallel to a distal resection plane for the femur.

Figure 12A:
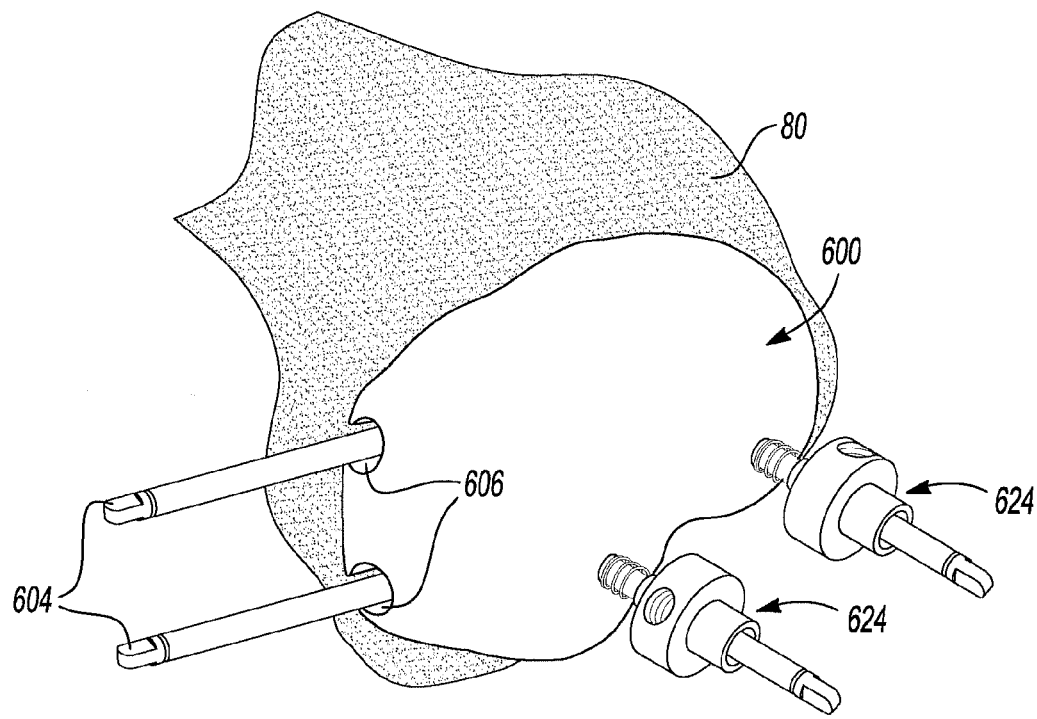
FIG. 12A is a perspective view of the femoral alignment guide of FIG. 11C shown after the removal of the drill guide.
Figure 12B:
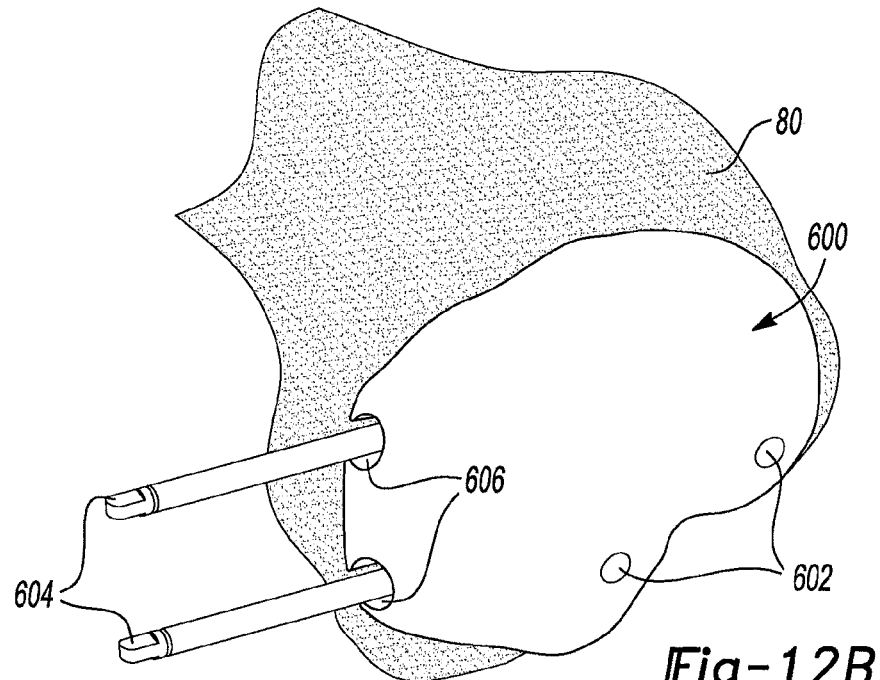
FIG. 12B is a perspective view of the femoral alignment guide of FIG. 12A shown after the removal of the spring pins.

Referring to FIG. 12A, the drill guide 700 can be removed. Referring to FIGS. 12B-13B, the fasteners 624 can be removed, and the alignment guide 600 can be removed from the femur 80 by sliding the alignment guide 600 off the guide elements 604 through the open portions 608 of the guiding apertures 606 without removing the guide elements 604 at the anterior/medial corner of the knee, at aspect 230 of FIG. 6.

The guide elements 604 can be used to prepare the joint surfaces for the prosthesis by mounting cutting guides/blocks for resecting the joint surface. Alternatively, a robotic arm or other automated, guided or computer controlled device that can guide the resections based on the pre-operative surgical plan can be mounted on the guide elements 604 and assist the surgeon in preparing the joint surface for the prosthesis.

Figure 14A:
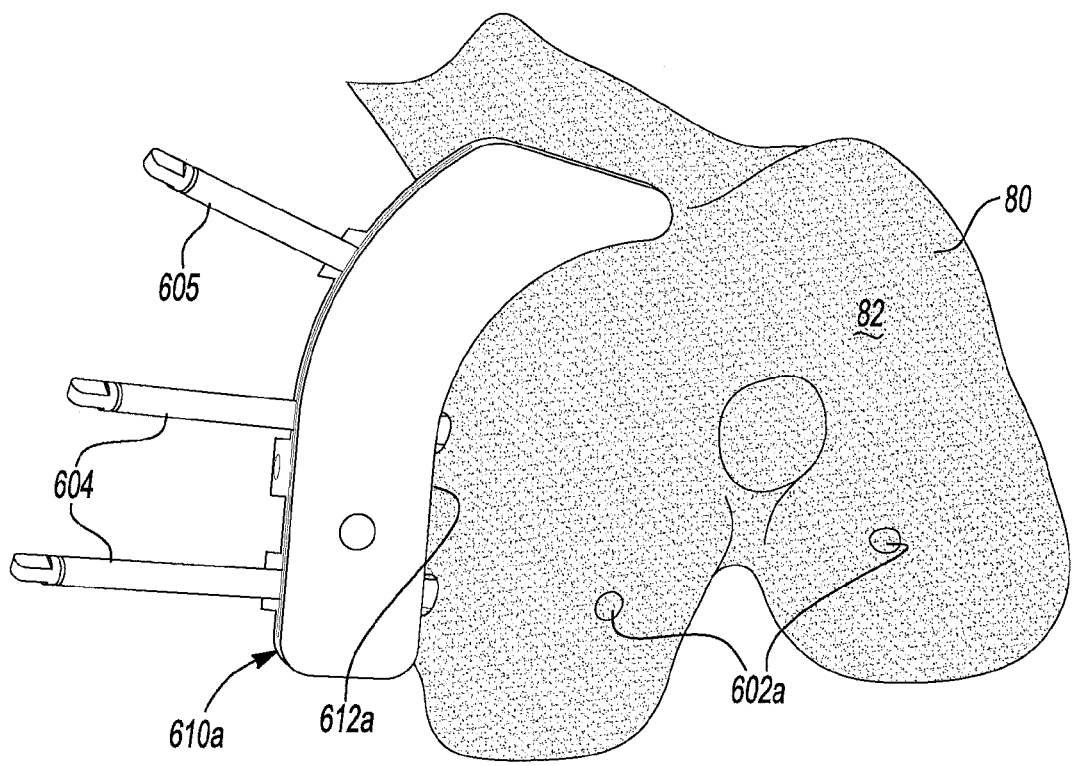
FIG. 14A is a perspective view of distal femoral cutting block shown over two pins on a patient's femur, according to the present teachings.
Figure 14B:
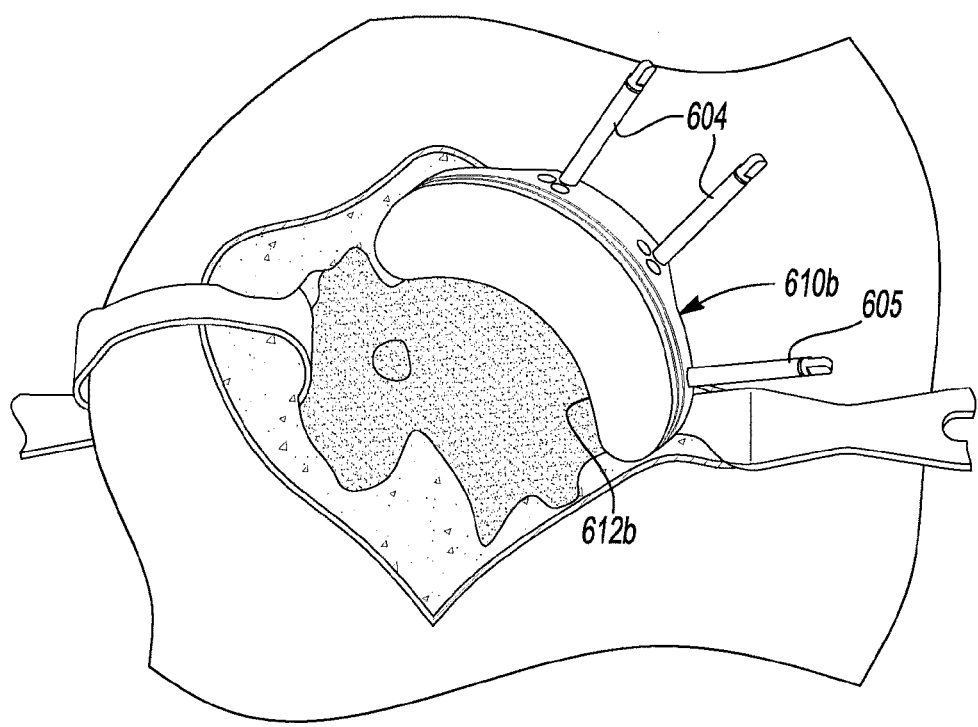
FIG. 14B is a perspective view of distal femoral cutting block shown over two guide pins on a patient's femur, according to the present teachings.

Referring to FIGS. 14A and 14B, exemplary distal cutting blocks 610a, 610b that can be mounted over the guide element 604 for making the distal resection, at aspect 640 of FIG. 6, are illustrated. A third fixation element 605, obliquely oriented relative to the guide elements 604 can also be used. The distal cutting blocks 610a, 610b can have an inner surface 612a, 612b that generally follows the shape of the femur 80 to a lesser or greater degree. The distal cutting blocks 610a, 610b can be disposable or re-usable.

Figure 15A:
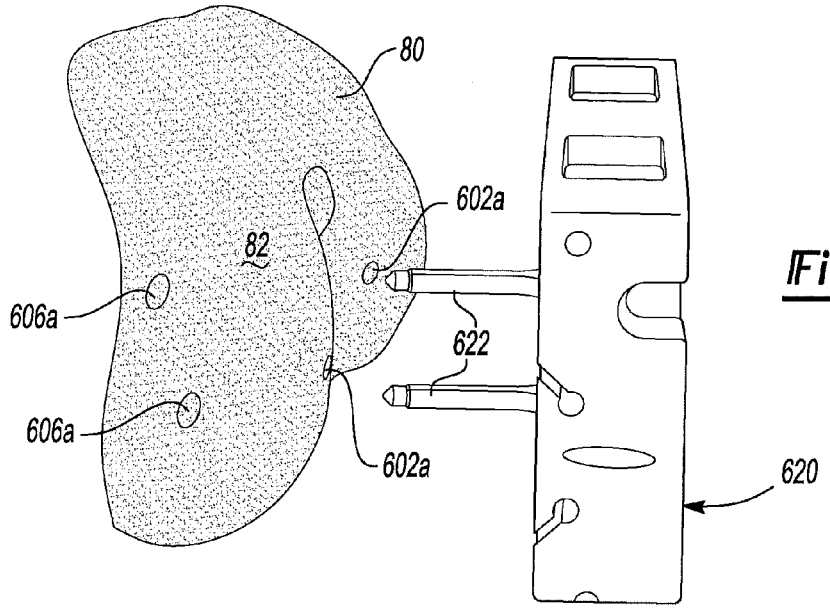
FIG. 15A is a perspective view of an exemplary 4-in-1 cutting block positioned on the femur with reference to holes corresponding to the spring pins.
Figure 15B:
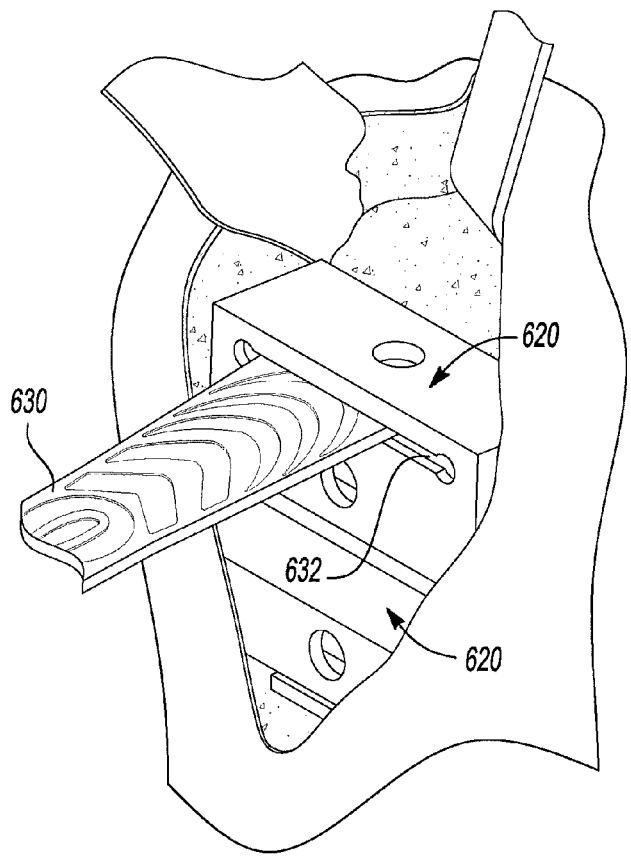
FIG. 15B a perspective view of the cutting block of FIG. 15A shown with a cutting blade.

Referring to FIGS. 15A and 15B, after the distal resections are made with the distal cutting block 610a or 610b, the femoral resection block 620 can be mounted with pegs or other supporting elements 622 into the holes 602a corresponding to the fasteners 624. The femoral resections can be made using, for example, a cutting blade 630 through slots 632 of the femoral resection block 620, at aspect 250 of FIG. 6.

Referring to FIGS. 6 and 16A-D, an exemplary alignment guide 600 is illustrated in connection with the patient's tibia 81. Reference numbers 260-300 relate to aspects of the method of FIG. 6 and are described in connection with the instruments shown in FIGS. 16A-16D for the tibia.

Figure 16A:
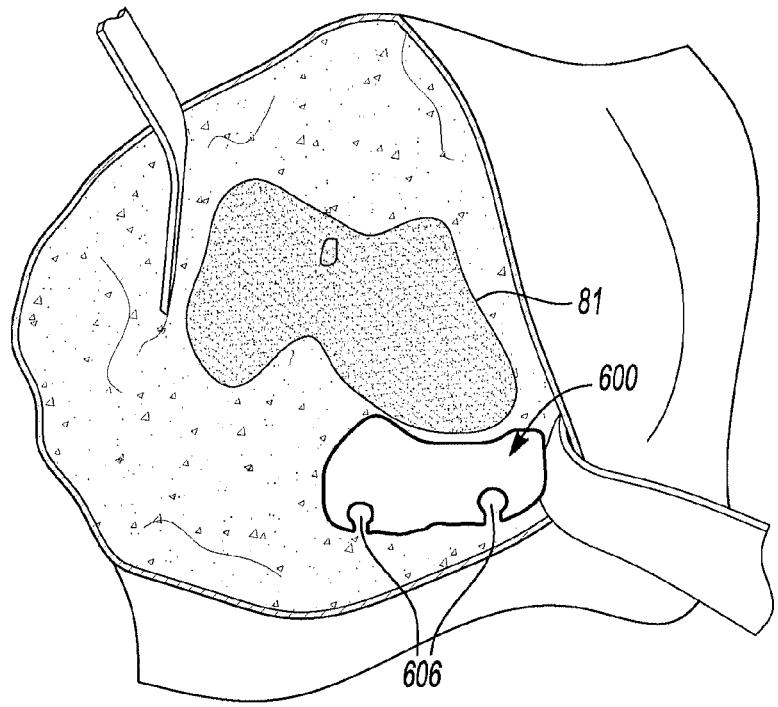
FIG. 16A is a perspective view of a tibial alignment guide according to the present teachings, shown mounted on the tibia.
Figure 16B:
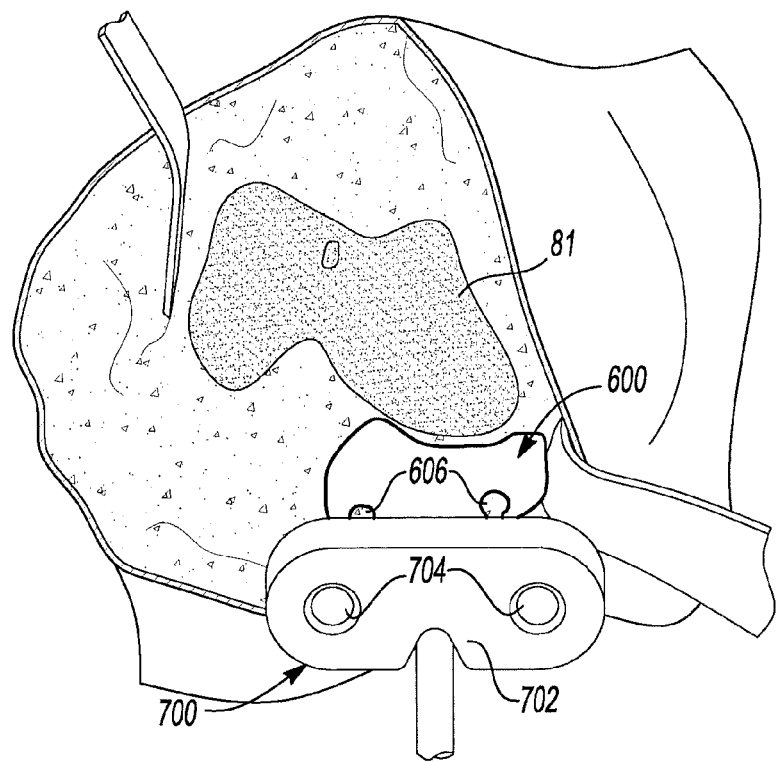
FIG. 16B is a perspective view of the tibial alignment guide of FIG. 16A shown with a drill guide.
Figure 16C:
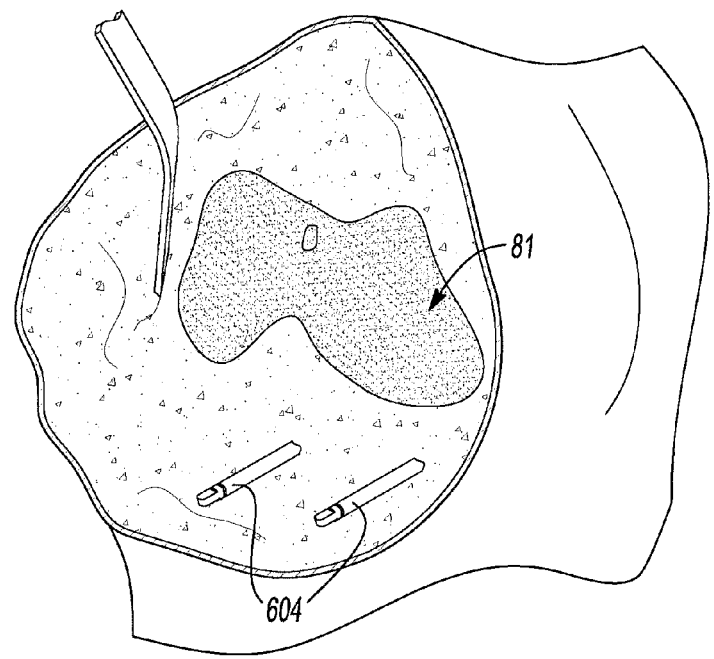
FIG. 16C is a perspective view of FIG. 16B illustrating the guide pins after the removal of the tibial alignment guide.
Figure 16D:
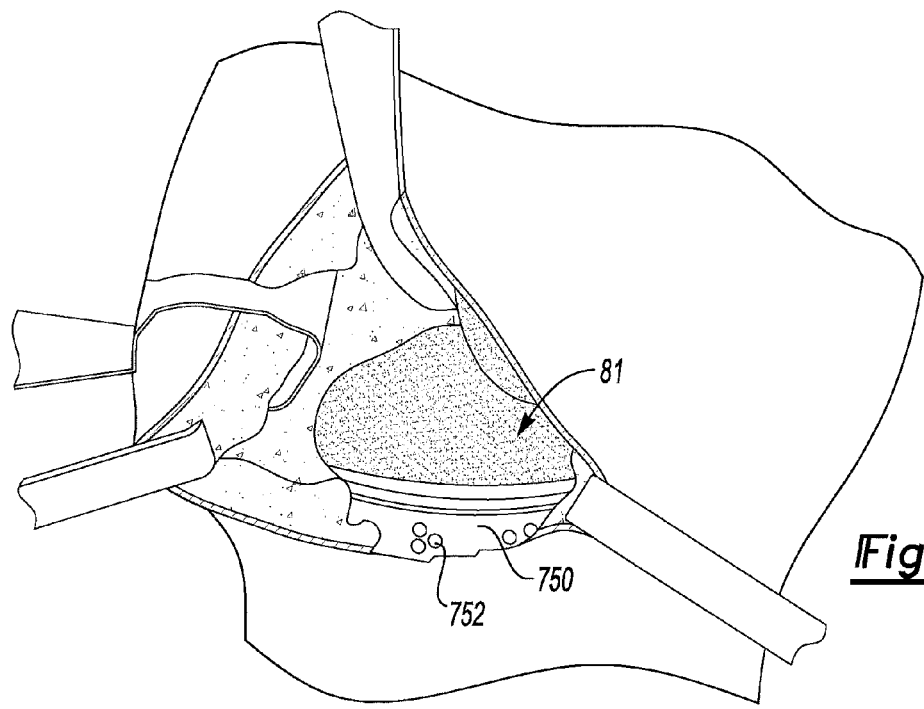
FIG. 16D is a perspective view of FIG. 16C illustrating a tibial cutting guide mounted on the guide pins.

The alignment guide 600 can conform, nestingly mate in three-dimensional space and snap on or "lock" by design onto the tibia 81 in a unique position, at aspect 260 of FIG. 6. The alignment guide 600 can wrap around the anterior-medial edge of the tibia 81, as shown in FIG. 16A. The drill guide 700 can be aligned with the counter-bored guiding apertures 606 of the alignment guide 600, as shown in FIG. 16B. Two or more guide elements 604 can be placed on the anterior medial side of the tibia, at aspect 270 of FIG. 6. An additional fixation element can also be used for additional securing for the alignment guide 600. The drill guide 700 and the alignment guide 600 can be removed, leaving behind the guide elements 604 attached, at aspect 280 of FIG. 6, and as shown in FIG. 16C. A disposable or reusable tibial cutting block 750 can be slid over the guide elements 604, at aspect 290 of FIG. 6, and as shown in FIG. 16D. The tibial cutting block 750 can include a series of holes 752, allowing the cutting block 750 to be translated proximally or distally to adjust the level of the distal resection. The tibial resection can be made, at 300.

The present teachings provide patient-specific alignment guides that can be used for alignment in orthopedic surgery. Each alignment guide includes an inner surface that nestingly mates and conforms in three-dimensional space with a corresponding joint surface of a specific patient. The alignment guides can be used for locating guide elements on the joint surface. After the alignment guides are removed, cutting guides or other cutting devices, including automated or robotic devices, can be mounted on the guide elements for making various resection cuts. Because the alignment guides are not used for cutting, the alignment guides do not require substantive thickness to extend anteriorly, and consequently have a lower profile, and less weight. Additionally, because the alignment guides are removed before cutting, the present teachings provide increased ability to visualize the cuts and the cutting process.

The preoperative plan and the alignment guides can provide a known starting point for the surgeon in the event that intra-operative changes are desired by the surgeon. The preoperative plan can be intra-operatively changed by the surgeon by using an adjustable resection device 800 having a cutting guide 806, such as the device disclosed in co-pending patent application Ser. No. 11/363,548, filed on Feb. 27, 2006, which is incorporated herein by reference and discussed below in reference with FIGS. 17-22. During the surgical procedure, the adjustable resection guide 800 can be mounted on the distal femur 80 using supporting elements 622, such as fasteners 624, pins or guide elements 604 through the locating holes 602a, 602b illustrated in FIGS. 15A and 15B. After soft tissue adjustment, the surgeon may intra-operatively adjust the surgical plan by changing the orientation of the femoral resection planes, for example. The cutting guide 806 of the adjustable resection guide 800 can be rotationally and translationally moved relative to the femur, and can be used to perform the modified resections. Alternatively, the adjustable resection device 800 can be used to drill new location holes 602a, 602b in new positions on the femur. The new holes 602a, 602b can be used to support a cutting block 620, as discussed in reference with FIGS. 15A and 15B.

Figure 17:
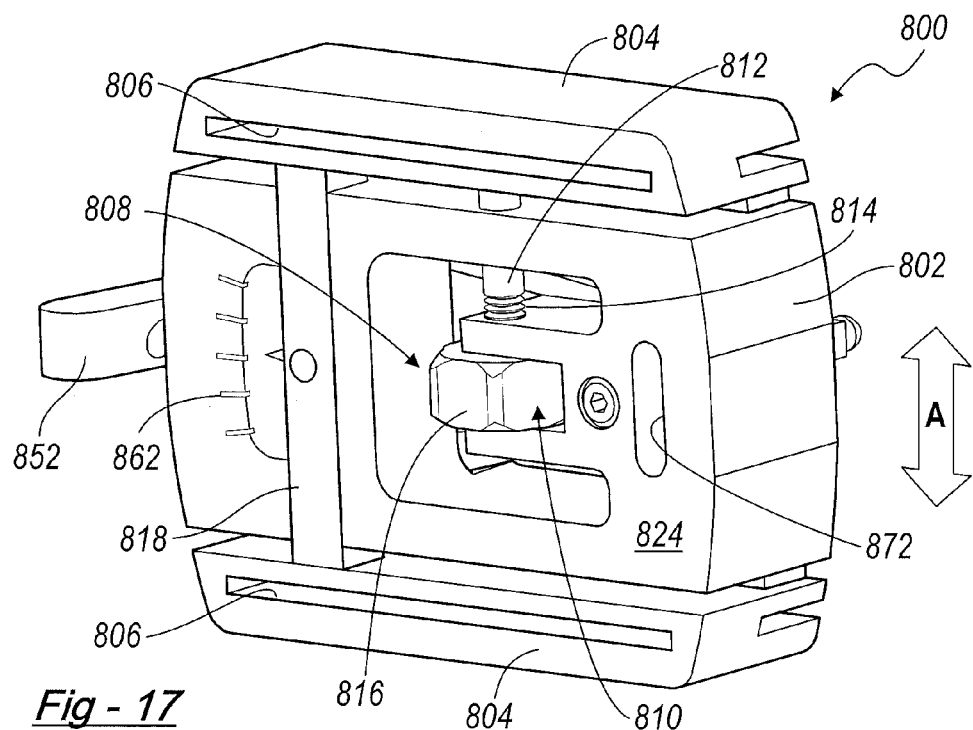
FIG. 17 is a front isometric view of a adjustable resection device according to the present teachings.
Figure 17A:
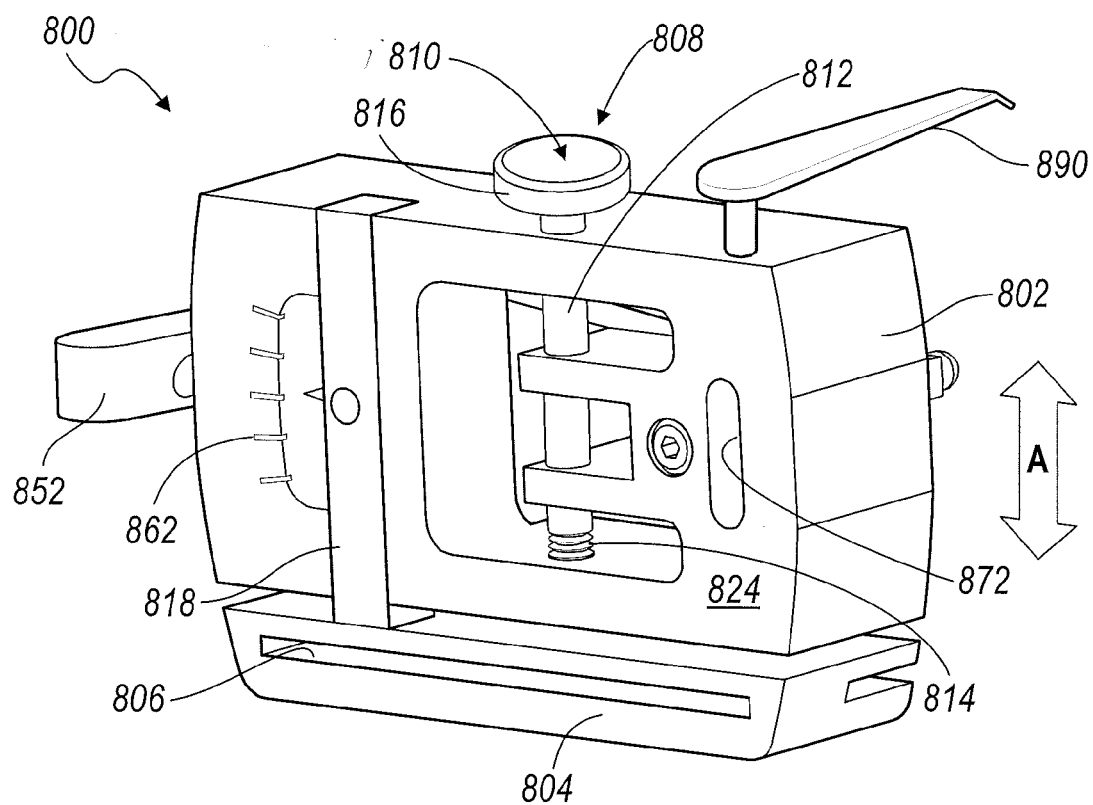
FIG. 17A is a front isometric view of a adjustable resection device according to the present teachings.
Figure 19:
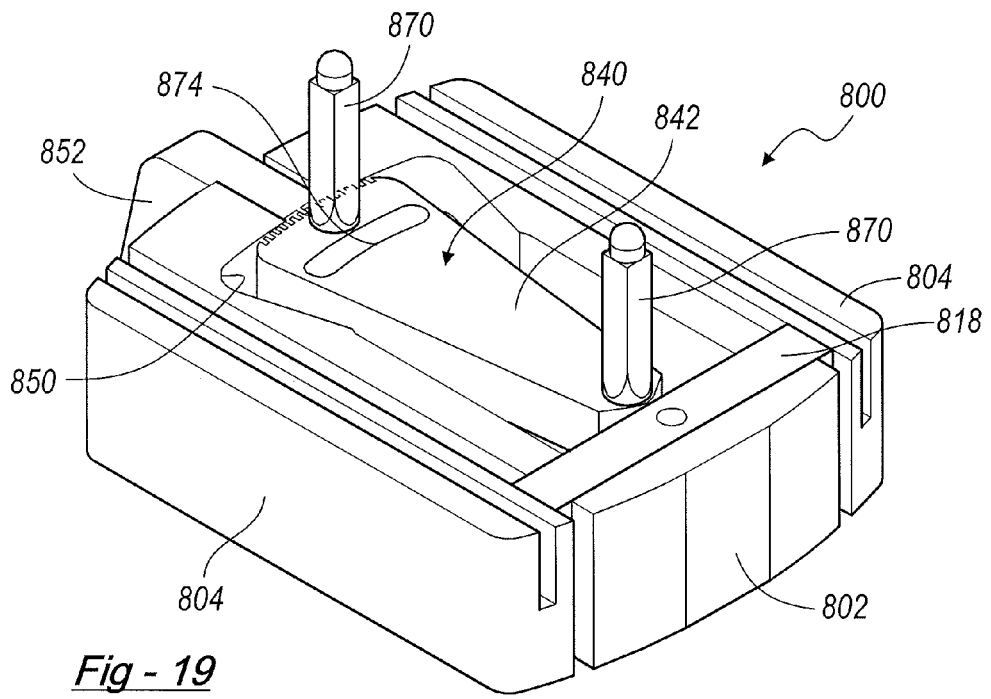
FIG. 19 is another rear isometric view of the adjustable resection device of FIG. 17.

Referring to FIGS. 17-22, an exemplary adjustable resection device 800 can include a body 802 attachable to a resected surface of a distal femur, and at least one cutting member 804 coupled to the body 802 and defining a cutting guide 806, such as, for example, a slot, or an edge or other appropriate guide for cutting with a saw blade or other cutting instrument. Two cutting members 804 are illustrated in FIG. 17 and are disposed on opposite sides of the body 802 such that the adjustable resection device 800 can be used selectively to make, for example, posterior cuts for the distal femur of the left or right knee by an appropriate 180-degree rigid body rotation. It will be appreciated, however, that the adjustable resection device 800 can also be used to make anterior, posterior, chamfer and other cuts in either the right or the left knee, as determined by the surgeon, and by appropriate rigid body rotations and relative adjustments. FIG. 17A illustrates an exemplary adjustable resection device 800 having only one cutting member 804. Further, the cutting guide 806 can be defined directly in the body 802.

Figure 22:
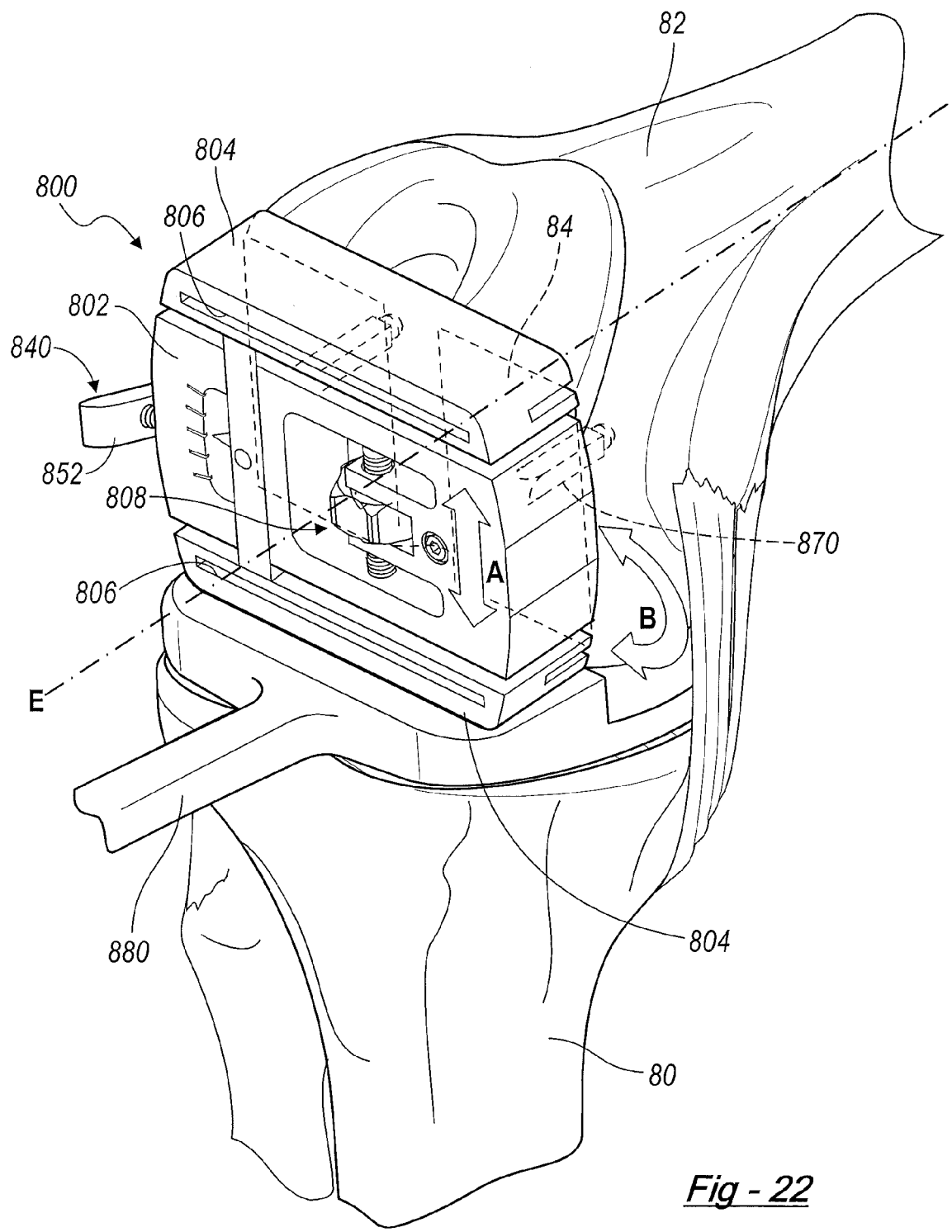
FIG. 22 is an environmental view of an adjustable resection device according to the present teachings.

The adjustable resection device 800 can include a linear adjustment mechanism 808 for adjusting a linear displacement of the cutting guide 806 relative to the resected surface of the distal femur in a direction substantially perpendicular to the cutting guide 806, as indicated by a double arrow "A", and corresponding to the anterior-posterior (A/P) direction. The linear adjustment mechanism 808 can include a linear actuator 810 for incrementally displacing the cutting guide 806 relative to the body 802 in the direction defined by the linear displacement. The linear actuator 810 can include a knob or nut 816 threadably coupled to a threaded portion 814 of a post 812 which is coupled to one of the cutting members 804, such that rotating the knob 816 clockwise or counterclockwise incrementally changes the position of the cutting guide 806 relative to the body 802. Linear displacements of 2 mm, for example, can be achieved in the directions indicated by the double arrow A and corresponding to the anterior or posterior surfaces of the distal femur, when the adjustable resection device 800 is mounted on a resected surface of the distal femur, as shown in FIG. 22. Other linear actuators 810 can be used to the same effect with cutting guides 106 defined in cutting members 804, and cutting guides 806 defined directly in the body 802, such as ratchet mechanisms, slide mechanism, guiding slots, etc.

Referring to FIGS. 18-22, the adjustable resection device 800 can include a rotational adjustment mechanism 840 for adjusting a rotational displacement of the cutting guide 806 relative to the resected surface of the femur. The rotational adjustment mechanism 840 can include a rotational member 842 having a first end 844 and a second end 846. The first end 844 can be narrower than the second end 846 such that the rotational member 842 can be tapered in width between its first and second ends 814, 846. The first end 844 can be pivotably coupled to the body 802 for rotation about an axis C perpendicular to the body 802. The rotational member 842 can be received in a recess 850 defined in the body 802 such that the rotational member 842 is substantially flush with or does not protrude outside of the second surface 826 of the body 802.

Figure 18:
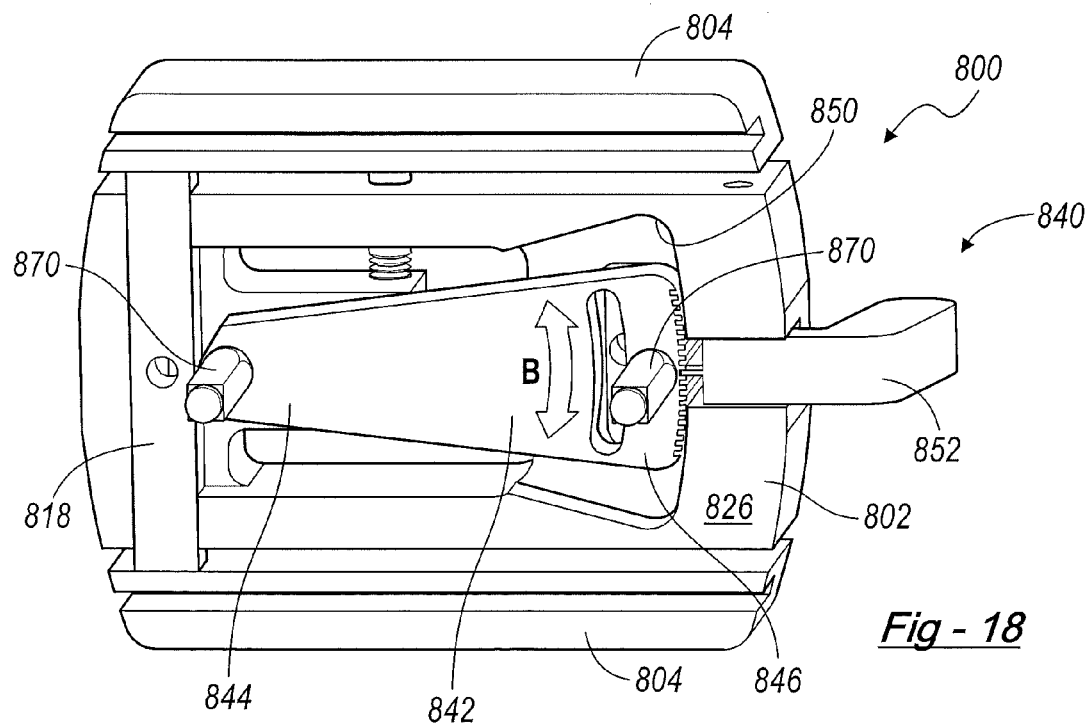
FIG. 18 is a rear isometric view of the adjustable resection device of FIG. 17.
Figure 20:
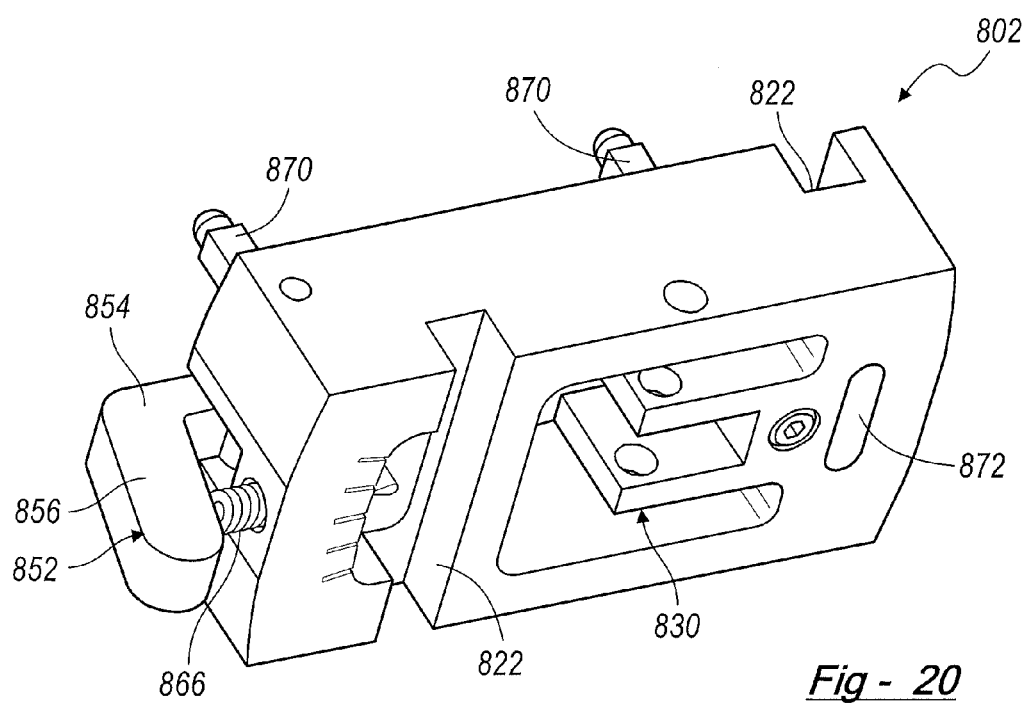
FIG. 20 is a front isometric view of the adjustable resection device of FIG. 17, shown without the linear adjustment mechanism.
Figure 21A:
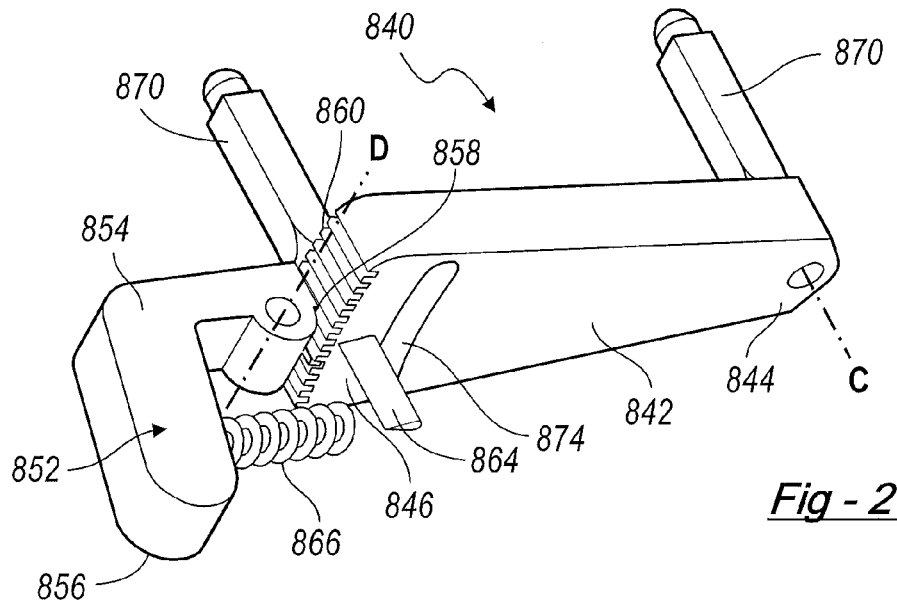
Figure 21B:
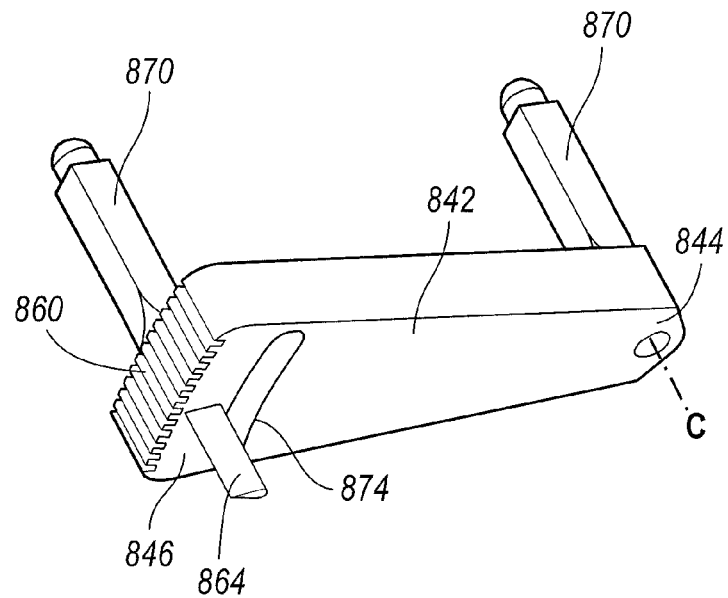

The second end 846 of the rotational member 842 can be releasably coupled to the body 802 for permitting rotation between the body 802 and the rotational member 842 about the first end 844 of the rotational member 842, as indicated by the curved double arrow "B" in FIG. 18, by the operation of a lever 852. The lever 852 can be rotationally coupled to the body 802 for rotation about an axis D, shown in FIG. 21A. The lever 852 can include first and second portions 854, 856 arranged in an L-shape configuration. The first portion 854 can include a ridge or flange or other engagement member 858 capable of engaging any one of a plurality of slots or grooves or other engagement receivers 860 that are shaped and configured to receive the engagement member 858, such that the rotational member 842 can be held in a plurality of orientations relative to the body 802. These orientations can be indicated on a scale 862 marked on the first surface 824 of the body 802 by an indicator 864 attached to the rotational member 842. The lever 852 is biased in an engagement position that prevents relative rotation between the rotational member 842 and the body 802 by a spring, coil or other biasing member 866. The biasing member 866 is coupled between the main body 802 and the second portion 856 of the lever 852, as shown in FIGS. 20 and 21A. Pressing the lever 852 towards the body 802 compresses the biasing member 866 and causes the lever 852 to rotate, thereby disengaging the engagement member 858 from the engagement receiver 860 and allowing relative rotation between the rotational member 842 and the body about axis C. Because the cutting members 804 are supported on and rotate with the body 802, the direction of the cutting guides 806 relative to the rotational member 842 can be accordingly rotationally adjusted.

The linear adjustment mechanism 808 and the rotational adjustment mechanism 840 together define a two-degree of freedom adjustment mechanism for one or two cutting guides 806 of the adjustable resection/cutting block device 800. The adjustable resection device 800 can be used in knee procedures to balance the flexion gap before various femoral cuts are made for inserting a knee implant. As known in the art, too small flexion gap can result in loss of motion, while too large flexion gap can result in instability. The flexion gap can be measured by placing one or more spacer blocks 880 of increasing thickness on the resected tibia in the flexion gap, as shown in FIG. 22.

Linear adjustments in the A/P (anterior-posterior) direction as well as rotational adjustments can be made as described above using the linear and rotational adjustment mechanisms 808, 840, respectively, until the flexion gap is balanced and matched with the extension gap, and the medial and lateral ligaments of the knee joint are appropriately tensioned. For example, if the medial and lateral ligaments are equally too lax, linear adjustment is made to reduce the flexion gap and move the cutting guides 806 in the A/P direction closer to the body. If the medial and lateral ligaments are equally too taut, linear adjustment can be made to increase the flexion gap and move the cutting guides 806 in the A/P direction away from the body 802. If the medial and lateral ligaments are unequally tensioned, rotational adjustments can be made relative to the longitudinal axis E of the distal femur (substantially perpendicularly to the resected surface of the distal femur), until the medial and lateral ligaments are equally tensioned, resulting in a balanced flexion gap. A posterior cut or at least one cut can then be performed through one of the cutting guides 806, as appropriate for the right or left knee.

It will be appreciated that the adjustable resection device 800 can be used to make posterior, anterior, chamfer or other cuts in either knee after balancing the flexion gap of the particular knee, and as determined by the operating surgeon. The adjustable resection device 800 can include an adjustment mechanism (808 and 840) operable to provide adjustment in two degrees of freedom for balancing the flexion gap. The two-degrees-of-freedom adjustments include a linear adjustment and a rotational adjustment. In posterior stabilized knee arthroplasty, for example, the linear adjustment can be in the A/P direction, and the rotational adjustment can be about the longitudinal axis E of the distal femur as shown in FIG. 22. The adjustable resection device 800 can be used to guide drilling holes into the distal femur for properly attaching other cutting blocks or cutting guides after a posterior or other cut is made and the adjustable resection device 800 is removed. The adjustable resection or cutting block device 800 can also be used for A/P sizing using the stylus 890, as shown in FIG. 17A.

The foregoing discussion discloses and describes merely exemplary arrangements of the present teachings. One skilled in the art will readily recognize from such discussion, and from the accompanying drawings, that various changes, modifications and variations can be made therein without departing from the spirit and scope of the present teachings.

What is claimed is:

1. A method of preparing a joint for a prosthesis in a patient, the method comprising:
   securing a patient-specific alignment guide to a joint surface of the patient, the patient-specific alignment guide having an inner three-dimensional surface configured to conform and mate in nesting relationship with the joint surface of the patient according to a preoperative surgical plan for the patient;
   attaching a guide element through the alignment guide to the joint surface;
   removing the alignment guide without removing the guide element;
   supporting an adjustable cutting block having a body and an adjustable cutting guide on the guide element;
   intraoperatively modifying the preoperative surgical plan of the patient by adjusting an orientation of the cutting guide relative to the body of the cutting block by rotating a rotational member, the rotational member pivotably coupled to the body of the adjustable cutting block at a first end and releasably connected to the body of the adjustable cutting block at a second end; and
   resecting the joint surface using the adjustable cutting block.

2. The method of claim 1, further comprising intraoperatively changing the preoperative plan of the patient by linearly displacing the cutting guide relative to the body of the adjustable cutting block using a linear adjustment mechanism of the adjustable cutting block.

3. The method of claim 2, further comprising incrementally displacing the cutting guide relative to the body of the adjustable cutting block using a linear actuator.

4. The method of claim 1, wherein attaching a guide element through the alignment guide to the joint surface includes passing the guide element through a guiding aperture of the alignment guide.

5. A method of preparing a knee joint for a prosthesis in a patient, the method comprising:
   mating a patient-specific femoral alignment guide onto a femoral joint surface of the patient, the femoral alignment guide configured to nestingly conform in a unique position on the femoral joint surface of the patient based on a three-dimensional image of the knee-joint of the patient created during a preoperative surgical plan from scans of the knee joint of the patient;
   drilling a first locating hole into the femoral joint surface through the femoral alignment guide
   inserting a first guide element into the first locating hole;
   removing the femoral alignment guide without removing the first guide element;
   supporting an adjustable resection device having a body and a cutting guide on the first guide element;
   intraoperatively modifying the preoperative surgical plan of the patient by adjusting the orientation of the cutting guide relative to the resection device by rotating a rotational member, the rotational member pivotably coupled to the body of the adjustable resection device at a first end and releasably connected to the body of the adjustable resection device at a second end;
   drilling a second locating hole into the femoral joint surface through the adjustable resection device;
   inserting a second guide element into the second locating hole;
   removing the adjustable resection device;
   supporting a cutting block on the second guide element; and
   resecting the femoral joint surface using the cutting block.

6. A method of preparing a knee joint for a prosthesis in a patient, the method comprising:
   mating a patient-specific femoral alignment guide onto a femoral joint surface of the patient, the patient-specific alignment guide nestingly conforming in a unique position on the femoral joint surface of the patient in three-dimensional space according to a preoperative surgical plan based on scans of the knee joint of the patient;

inserting first and second guide elements through first and second resection-guiding apertures of the femoral alignment guide into the femoral joint surface;

removing the femoral alignment guide without removing the first and second guide elements;

supporting an adjustable resection device having a body and an adjustable cutting guide on the first and second guide elements;

intraoperatively modifying the preoperative surgical plan by adjusting a position of the cutting guide relative to the adjustable resection device by rotating a rotational member pivotably coupled to the body of the adjustable resection device at a first end and releasably connected to the body of the adjustable resection device at a second end; and resecting the femoral joint surface.

7. The method of claim 6, further comprising linearly displacing the cutting guide using a linear adjustment mechanism of the adjustable resection device.

8. The method of claim 6, wherein the cutting guide comprises a guiding slot for guiding a resection.

9. The method of claim 6, wherein the cutting guide comprises first and second guiding slots for selectively resecting a right or left knee.

10. The method of claim 6, further comprising incrementally displacing the cutting guide relative to the body by a linear displacement.

11. The method of claim 10, further comprising rotating a knob threadably coupled to a cutting member that supports the cutting guide.

12. The method of claim 6, further comprising pressing a lever coupled to the rotational member for enabling pivoting of the rotational member.

13. The method of claim 12, further comprising biasing the lever in an engagement position preventing rotation between the rotational member and the body.

* * * * *

UNITED STATES PATENT AND TRADEMARK OFFICE
CERTIFICATE OF CORRECTION

| | | |
|---|---|---|
| PATENT NO. | : 8,070,752 B2 | Page 1 of 1 |
| APPLICATION NO. | : 11/971390 | |
| DATED | : December 6, 2011 | |
| INVENTOR(S) | : Metzger et al. | |

It is certified that error appears in the above-identified patent and that said Letters Patent is hereby corrected as shown below:

Column 2, Line 22, delete "view" insert --views--.

Column 2, Line 24, delete "view" insert --views--.

Column 2, Line 32, after "is" insert --a--.

Column 2, Line 40, delete "illustrated" insert --illustrates--.

Column 2, Line 42, after "of" insert --a--.

Column 2, Line 45, after "of" insert --a--.

Column 2, Line 51, after "15B" insert --is--.

Column 2, Line 58-59, delete second occurrence of paragraph "FIG. 16B is a perspective view of the tibial alignment guide of FIG. 16A shown with a drill guide".

Column 2, Line 64, delete "a adjustable" insert --an adjustable--.

Column 2, Line 66, delete "a adjustable" insert --an adjustable--.

Column 10, Line 41, after "guide" insert --;--.

Signed and Sealed this
Twenty-eighth Day of February, 2012

David J. Kappos
*Director of the United States Patent and Trademark Office*